(12) United States Patent
Knudson et al.

(10) Patent No.: US 7,489,969 B2
(45) Date of Patent: ***Feb. 10, 2009

(54) VAGAL DOWN-REGULATION OBESITY TREATMENT

(75) Inventors: Mark B. Knudson, Shoreview, MN (US); Richard R. Wilson, Arden Hills, MN (US); Katherine S. Tweden, Mahtomedi, MN (US); Timothy R. Conrad, Eden Prairie, MN (US)

(73) Assignee: EnteroMedics Inc., St. Paul, MN (US)

( * ) Notice: Subject to any disclaimer, the term of this patent is extended or adjusted under 35 U.S.C. 154(b) by 299 days.

This patent is subject to a terminal disclaimer.

(21) Appl. No.: 10/674,330

(22) Filed: Sep. 29, 2003

(65) Prior Publication Data
US 2004/0172086 A1 Sep. 2, 2004

Related U.S. Application Data

(63) Continuation-in-part of application No. 10/358,093, filed on Feb. 3, 2003, now abandoned.

(51) Int. Cl.
*A61N 1/18* (2006.01)
(52) U.S. Cl. ...................................................... 607/40
(58) Field of Classification Search ................. 607/2–3, 607/40–41, 45–46, 48, 63; 606/20–26; 604/890.1, 604/891.1, 892.1, 19–21
See application file for complete search history.

(56) References Cited

U.S. PATENT DOCUMENTS

| | | | |
|---|---|---|---|
| 3,128,760 A | 4/1964 | Baker | |
| 3,411,507 A | 11/1968 | Wingrove | |
| 4,114,625 A | 9/1978 | Onat | |
| 4,198,963 A | 4/1980 | Barkalow et al. | |
| 4,702,254 A | 10/1987 | Zabara | |
| 4,776,349 A | 10/1988 | Nashef et al. | |
| 4,867,164 A | 9/1989 | Zabara | |
| 5,025,807 A | 6/1991 | Zabara | |

(Continued)

FOREIGN PATENT DOCUMENTS

EP 1 666 087 A1 2/1998

(Continued)

OTHER PUBLICATIONS

Gui, D. et al. "Botulinum toxin injected in the gastric wall reduces body weight and food intake in rats" Aliment Pharmacol Ther 2000; 14: 829-834.*

(Continued)

*Primary Examiner*—Kennedy J. Schaetzle
*Assistant Examiner*—Jessica Reidel
(74) *Attorney, Agent, or Firm*—Katherine M. Kowalchyk; Merchant & Gould P.C.

(57) ABSTRACT

Obesity is treated by applying a non-ablative, non-systemic therapy to a vagus nerve of an obese patient at a site below a vagal innervation of a heart. The therapy is selected to at least partially down-regulate a neural activity on the vagus nerve of the obese patient. The therapy is applied in a manner to down-regulate at least afferent signals on the vagus nerve.

8 Claims, 8 Drawing Sheets

U.S. PATENT DOCUMENTS

| Patent No. | Date | Inventor(s) |
|---|---|---|
| 5,188,104 A | 2/1993 | Wernicke et al. |
| 5,199,430 A | 4/1993 | Fang et al. |
| 5,215,086 A | 6/1993 | Terry, Jr. et al. |
| 5,226,429 A | 7/1993 | Kuzmak |
| 5,231,988 A | 8/1993 | Wernicke et al. |
| 5,263,480 A | 11/1993 | Wernicke et al. |
| 5,269,303 A | 12/1993 | Wernicke et al. |
| 5,292,344 A | 3/1994 | Douglas |
| 5,299,569 A | 4/1994 | Wernicke et al. |
| 5,330,515 A | 7/1994 | Rutecki et al. |
| 5,335,657 A | 8/1994 | Terry et al. |
| 5,344,438 A | 9/1994 | Testerman |
| 5,370,675 A | 12/1994 | Edwards et al. |
| 5,423,872 A | 6/1995 | Cigaina |
| 5,514,175 A | 5/1996 | Kim et al. |
| 5,540,730 A | 7/1996 | Terry, Jr. et al. |
| 5,571,150 A | 11/1996 | Wernicke et al. |
| 5,601,604 A | 2/1997 | Vincent |
| 5,620,955 A | 4/1997 | Knight et al. |
| 5,690,691 A | 11/1997 | Chen et al. |
| 5,707,400 A | 1/1998 | Terry, Jr. et al. |
| 5,716,385 A | 2/1998 | Mittal et al. |
| 5,747,060 A * | 5/1998 | Sackler et al. .............. 424/426 |
| 5,830,434 A | 11/1998 | Taylor et al. |
| 5,836,994 A | 11/1998 | Bourgeois |
| 5,861,014 A | 1/1999 | Familoni |
| 5,919,216 A | 7/1999 | Houben et al. |
| 5,967,977 A | 10/1999 | Mullis et al. |
| 5,995,872 A | 11/1999 | Bourgeois |
| 6,083,249 A | 7/2000 | Familoni |
| 6,091,992 A | 7/2000 | Bourgeois et al. |
| 6,093,167 A | 7/2000 | Houben et al. |
| 6,097,984 A | 8/2000 | Douglas |
| 6,098,629 A | 8/2000 | Johnson et al. |
| 6,104,955 A | 8/2000 | Bourgeois |
| 6,111,715 A | 8/2000 | Tsuchiya et al. |
| 6,129,726 A | 10/2000 | Edwards |
| 6,135,978 A | 10/2000 | Houben et al. |
| 6,148,222 A | 11/2000 | Ramsey, III |
| 6,216,039 B1 | 4/2001 | Bourgeois |
| 6,238,423 B1 | 5/2001 | Bardy |
| 6,243,607 B1 | 6/2001 | Mintchev et al. |
| 6,261,280 B1 | 7/2001 | Houben et al. |
| 6,261,572 B1 | 7/2001 | Donovan |
| 6,292,703 B1 | 9/2001 | Meier |
| 6,308,105 B1 | 10/2001 | Duysens et al. |
| 6,312,708 B1 * | 11/2001 | Donovan .................... 424/423 |
| 6,341,236 B1 | 1/2002 | Osorio et al. |
| 6,364,899 B1 * | 4/2002 | Dobak, III .................. 607/113 |
| 6,369,079 B1 * | 4/2002 | Rubin et al. ................. 514/327 |
| 6,405,732 B1 | 6/2002 | Edwards et al. |
| 6,449,511 B1 | 9/2002 | Mintchev et al. |
| 6,473,644 B1 | 10/2002 | Terry, Jr. et al. |
| 6,532,388 B1 | 3/2003 | Hill et al. |
| 6,558,708 B1 * | 5/2003 | Lin ............................ 424/490 |
| 6,571,127 B1 | 5/2003 | Ben-Haim et al. |
| 6,587,719 B1 | 7/2003 | Barrett et al. |
| 6,591,137 B1 | 7/2003 | Fischell et al. |
| 6,609,025 B2 | 8/2003 | Barrett et al. |
| 6,610,713 B2 | 8/2003 | Tracey |
| 6,611,715 B1 | 8/2003 | Boveja |
| 6,612,983 B1 | 9/2003 | Marchal |
| 6,622,038 B2 | 9/2003 | Barrett et al. |
| 6,684,105 B2 | 1/2004 | Cohen et al. |
| 6,746,474 B2 | 6/2004 | Saadat |
| 6,826,428 B1 | 11/2004 | Chen et al. |
| 6,832,114 B1 | 12/2004 | Whitehurst et al. |
| 6,853,862 B1 | 2/2005 | Marchal et al. |
| 6,895,278 B1 | 5/2005 | Gordon |
| 6,928,320 B2 | 8/2005 | King |
| 6,993,391 B2 | 1/2006 | Flesler et al. |
| 7,054,690 B2 | 5/2006 | Imran |
| 7,072,720 B2 | 7/2006 | Puskas |
| 7,076,307 B2 | 7/2006 | Boveja et al. |
| 7,142,910 B2 | 11/2006 | Puskas |
| 2001/0012828 A1 | 8/2001 | Aoki et al. |
| 2002/0032468 A1 | 3/2002 | Hill et al. |
| 2002/0052336 A1 | 5/2002 | Yerxa et al. |
| 2002/0055779 A1 | 5/2002 | Andrews |
| 2002/0072780 A1 | 6/2002 | Foley |
| 2002/0087192 A1 | 7/2002 | Barrett et al. |
| 2002/0103424 A1 | 8/2002 | Swoyer et al. |
| 2002/0161360 A1 * | 10/2002 | Carroll ........................ 606/21 |
| 2002/0198570 A1 | 12/2002 | Puskas |
| 2002/0198571 A1 | 12/2002 | Puskas |
| 2003/0014086 A1 | 1/2003 | Sharma |
| 2003/0018367 A1 | 1/2003 | DiLorenzo |
| 2003/0040785 A1 | 2/2003 | Maschino et al. |
| 2003/0045909 A1 | 3/2003 | Gross et al. |
| 2003/0045914 A1 * | 3/2003 | Cohen et al. .................. 607/62 |
| 2003/0144709 A1 | 7/2003 | Zabara et al. |
| 2003/0171789 A1 | 9/2003 | Malek et al. |
| 2003/0181958 A1 | 9/2003 | Dobak, III |
| 2003/0181959 A1 | 9/2003 | Dobak, III |
| 2003/0195601 A1 | 10/2003 | Hung et al. |
| 2003/0212440 A1 | 11/2003 | Boveja |
| 2004/0039425 A1 | 2/2004 | Greenwood-Van Meerveld |
| 2004/0059383 A1 | 3/2004 | Puskas |
| 2004/0086531 A1 | 5/2004 | Barron |
| 2004/0089313 A1 * | 5/2004 | Utley et al. .................. 128/898 |
| 2004/0127953 A1 | 7/2004 | Kilgore et al. |
| 2004/0167583 A1 * | 8/2004 | Knudson et al. .............. 607/40 |
| 2004/0172085 A1 | 9/2004 | Knudson et al. |
| 2004/0172088 A1 * | 9/2004 | Knudson et al. .............. 607/40 |
| 2004/0176812 A1 | 9/2004 | Knudson et al. |
| 2004/0181178 A1 | 9/2004 | Aldrich et al. |
| 2004/0193229 A1 | 9/2004 | Starkebaum et al. |
| 2004/0236381 A1 | 11/2004 | Dinsmoor et al. |
| 2004/0236382 A1 | 11/2004 | Dinsmoor et al. |
| 2004/0249416 A1 | 12/2004 | Yun et al. |
| 2005/0038484 A1 * | 2/2005 | Knudson et al. .............. 607/40 |
| 2005/0049655 A1 | 3/2005 | Boveja et al. |
| 2005/0070970 A1 | 3/2005 | Knudson et al. |
| 2005/0070974 A1 | 3/2005 | Knudson et al. |
| 2005/0075693 A1 | 4/2005 | Toy et al. |
| 2005/0131485 A1 * | 6/2005 | Knudson et al. .............. 607/40 |
| 2005/0137644 A1 | 6/2005 | Boveja et al. |
| 2005/0143378 A1 | 6/2005 | Yun et al. |
| 2005/0143412 A1 | 6/2005 | Puskas |
| 2005/0143787 A1 | 6/2005 | Boveja et al. |
| 2005/0149141 A1 | 7/2005 | Starkebaum |
| 2005/0149146 A1 | 7/2005 | Boveja et al. |
| 2005/0149148 A1 | 7/2005 | King |
| 2005/0203501 A1 | 9/2005 | Aldrich et al. |
| 2005/0240231 A1 | 10/2005 | Aldrich et al. |
| 2006/0015151 A1 | 1/2006 | Aldrich |
| 2006/0036293 A1 | 2/2006 | Whitehurst et al. |
| 2006/0212089 A1 | 9/2006 | Tass et al. |

FOREIGN PATENT DOCUMENTS

| | | |
|---|---|---|
| EP | 1 004 330 A1 | 5/2000 |
| EP | 865800 | 9/2004 |
| WO | WO 01/41671 A2 | 6/2001 |
| WO | WO 01/43821 A1 | 6/2001 |
| WO | WO 02/26320 A1 | 4/2002 |
| WO | WO02/065896 | 8/2002 |
| WO | WO-02/065896 A2 * | 8/2002 |
| WO | WO 2004/064918 A1 | 8/2004 |

WO  WO 2004/082763 A1  9/2004

OTHER PUBLICATIONS

Aggarwal A, et al., "Predominant Symptoms in Irritable Bowel Syndrome Correlate with Specific Autonomic Nervous system Abnormalities", *Gastroenterol*, (1994);106:945-950.

Amaris et al., "Microprocessor controlled movement of solid colonic content using sequential neural electrical stimulation", *Gut*, 50: pp. 475-479 (2002).

Batterham, et al., "Inhibition of Food Intake in Obese Subjects by Peptide YY3-36", *New England J. Med.*, pp. 941-948 (Sep. 4, 2003).

Cann PA, et al. "Irritable Bowel Syndrome: Relationship of Disorders in the Transit of a Single Solid Meal to Symptoms Patterns", *Gut*, (1981);24:405-411.

Cuomo R, et al., "Functional Dyspepsia Symptoms, Gastric Emptying and Satiety Provocation Test: Analysis of Relationships", *Scand J Gastroenterol*, (2001) 36:1030-1036.

Dapoigny et al., "Vagal influence on colonic motor activity in conscious nonhuman primates", *Am. J. Physiol.*, 262: G231-G236 (1992).

Drossman, "Rome II: A Multinational Consensus Document on Gastrointestinal Disorders—The Functional Gastrointestinal Disorders and the Rome II Process", *Gut*, vol. 45 (Suppl II):111-115 (1999).

Evans PR, et al., "Gastroparesis and Small Bowel Dysmotility in Irritable Bowel Syndrome", *Dig Dis Sci* (1997);42:2087-2093.

Evans PR, et al., "Jejunal Sensorimotor Dysfunction in Irritable Bowel Syndrome: Clinical and Psychosocial Features", *Gastroenterol*, (1996);110:393-404.

Gershon, "The Second Brain", Harper Collins Publishers, Inc, New York, NY p. 19 (1998).

Guyton AC, et al., "Propulsion and Mixing of Food in the Alimentary Tract", Textbook of Medical Physiology, $10^{th}$ ed. Philadelphia: W. B. Saunders and Company, 200:728-737.

Guyton AC, et al., "Secretory Functions of the Alimentary Tract", Textbook of Medical Physiology, $10^{th}$ ed. Philadelphia: W. B. Saunders and Company, 200:738-753.

Hausken, et al., "Low Vagal Tone and Antral Dysmotility in Patients with Functional Dyspepsia", *Psychosomatic Medicine*, 55: 12-22 (1993).

Heitkemper, et al., "Evidence for Automatic Nervous System Imbalance in Women with Irritable Bowel Syndrome", *Digestive Diseases and Sciences*, vol. 43, No. 9, pp. 2093-2098 (1998).

Hjelland, et al., "Vagal tone and meal-induced abdominal symptoms in healthy subjects", *Digestion*, 65: 172-176 (2002).

Holst et al "Nervous control of pancreatic endocrine secretion in pigs" *Acta Physiol Scand*, (1981), 111:1-7.

Hornbuckle K, et al. "The Diagnosis and Work-Up of the Patient with Gastroparesis", *J Clin Gastroenterol*, (2000);30:117-124.

Kellow JE, et al., "Dysmotility of the Small Intestine in Irritable Bowel Syndrome", *Gut*, (1988);29:1236-1243.

Kellow JE, et al., "Rome II: A Multinational Consensus Document on Gastrointestinal Disorders—Principle of Applied Neurogastroenterology: Physiology/Motility-Sensation", *Gut*, (1999);45(Suppl II):1117-1124.

Korner et al., "To Eat or Not to Eat—How the Gut Talks to the Brain", *New England J. Med.*, pp. 926-928 (Sep. 4, 2003).

Lagergren J, et al., "Symptomatic Gastroesophageal Reflux as a Risk Factor for Esophageal Adenocarcinoma", *New Engl J Med*, (1999);340:825-831.

Lin et al., "Hardware—software co-design of portable functional gastrointestinal stimulator system", *J. of Medicine Eng. & Tech.*, vol. 27, No. 4 pp. 164-177 (2003).

Merio R, et al., "Slow Gastric Emptying in Type 1 Diabetes: Relation to Autonomic and Peripheral Neuropathy, Blood Glucose, and Glycemic Control", *Diabetes Care*, (1997);20:419-423.

Mintchev, et al., "Electrogastrographic impact of multi-site functional gastric electrical stimulation", *J. of Medical Eng. & Tech.*, vol. 23, No. 1 pp. 5-9 (1999).

Mittal RK, et al., "Mechanism of Disease: The Esophagogastric Junction", *New Engl J Med*, (1997);336:924-932.

Novartis product description, Zelnorm®, Jul. 2002 (T2002-19).

Paterson CA, et al., "Determinants of Occurrence and Volume of Transpyloric Flow During Gastric Emptying of Liquids in Dogs: Importance of Vagal Input", *Dig Dis Sci*, (2000);45:1509-1516.

Petrofsky, et al., "Impact of Recruitment Order on Electrode Design for Neural Prosthetics of Skeletal Muscle", *Am. J. of Physical Medicine*, vol. 60, No. 5, pp. 243-253 (1981).

Poelmans J, et al., "Prospective Study on the Incidence of Chronic Ear Complaints Related to Gastroesophageal Reflux and on the Outcome of Antireflux Therapy", *Ann Otol Rhinol Laryngol*, (2002);111:933-938.

Rashev et al., "Microprocessor-Controlled Colonic Peristalsis", *Digestive Diseases and Sciences*, vol. 47, No. 5, pp. 1034-1048 (2002).

Rashev, et al., "Three-dimensional static parametric modeling of phasic colonic contractions for the purpose of microprocessor-controlled functional stimulation", *J. of Medical Eng. & Tech.*, vol. 25, No. 3 pp. 85-96 (2001).

Sarnelli G, et al., "Symptoms Associated with Impaired Gastric Emptying of Solids and Liquids in Functional Dyspepsia", *Am J Gastroenterol*, (2003) 98:783-788.

Scheffer RC, et al., "Elicitation of Transient Lower Oesophageal Sphincter Relaxations in Response to Gastric Distension", *Neurogastroenterol Motil*, (2002);14:647-655.

Schmidt T, et al., "Ambulatory 24-Hour Jejunal Motility in Diarrhea-Predominant Irritable Bowel Syndrome", *J Gastroenterol*, (1996);31:581-589.

Schwartz MP, et al., "Chemospecific Alterations in Duodenal Perception and Motor Response in Functional Dyspepsia", *Am J Gastroenterol*, (2001);96:2596-2602.

Schwartz MP, et al., "Human Duodenal Motor Activity in Response to Acid and Different Nutrients", *Dig Dis Sci*, (2001);46:1472-1481.

Simren M, et al., "Abnormal Propagation Pattern of Duodenal Pressure Waves in the Irritable Bowel Syndrome (IBS)", *Dig Dis Sci*, (2000);45:2151-2161.

Solomonow, et al., "Control of Muscle Contractile Force through Indirect High-Frequency Stimulation", *Am. J. of Physical Medicine*, vol. 62, No. 2, pp. 71-82 (1983).

Sontag SJ, et al., "Asthmatics with Gastroesophageal Reflux: Long Term Results of a Randomized Trial of Medical and Surgical Antireflux Therapies", *Am J Gastroenterol*, (2003);98:987-999.

Stanghellini V, et al., "Risk Indicators of Delayed Gastric Emptying of Solids in Patients with Functional Dyspepsia", *Gastroenterol*, (1996) 110:1036-1042.

Tack J, et al., "Role of Impaired Gastric Accommodation to a Meal in Functional Dyspepsia", *Gastroenterol*, (1998) 115:1346-1352.

Tack J, et al., "Symptom Pattern and Gastric Emptying Rate Assessed by the Octanoic Acid Breath Test in Functional Dyspepsia" [abstract]. *Gastroenterol*, (1998) 114:A301.

Talley et al., "Rome II: A Multinational Consensus Document on Gastrointestinal Disorders—Functional Gastroduodenal Disorders" *Gut*, vol. 45 (Suppl II), pp. 137-1142 (1999).

Thompson WG, et al., "Rome II: A Multinational Consensus Document on Gastrointestinal Disorders—Functional Bowel Disorders and Functional Abdominal Pain", *Gut*, (1999) ;45(Suppl II):1143-1147.

Tougas, "The Autonomic Nervous System in Functional Bowel Disorders", *Gut*, vol. 47 (Suppl IV), pp. iv78-iv80 (2000).

Undeland KA, et al., "Wide Gastric Antrum and Low Vagal Tone in Patients with Diabetes Mellitus Type 1 Compared to Patients with Functional Dyspepsia and Healthy Individuals", *Dig Dis Sci*, (1996) 41:9-16.

Van Den Honert, et al., "Generation of Unidirectionally Propagated Action Potentials in a Peripheral Nerve by Brief Stimuli", *Science*, vol. 206, pp. 1311-1312.

Van Wijk HJ, et al., "Gastric Emptying and Dyspeptic Symptoms in the Irritable Bowel Syndrome", *Scand J Gastroenterol*, (1992);27:99-102.

Vassallo MJ, et al., "Colonic Tone and Motility in Patients with Irritable Bowel Syndrome", *Mayo Clin Proc*, (1992);67:725-731.

Wilmer A, et al., "Ambulatory Gastrojejunal Manometry in Severe Motility-like Dyspepsia: Lack of Correlation between Dysmotility, Symptoms and Gastric Emptying", *Gut*, (1998) 42:235-242.

Kilgore, K. et al., "Nerve Conduction Block Utilising High-Frequency Alternating Current," *Medical & Biological Engineering & Computing*, vol. 42, pp. 394-406 (2004).

Product Brochure, "Atrostim Phrenic Nerve Stimulator," AtroTech Oy, P.O. Box 28, FIN-33721 Tampere, Finland, 2 pages (Jun. 2004).

Accarino, et al, "Symptomatic Responses To Stimulation Of Sensory Pathways In The Jejunum", *Am. J. Physiol.*, vol. 263, pp. G673-G677 (1992).

Accarino, et al, "Selective Dysfunction Of Mechano Sensitive Intestinal Afferents In Irritable Bowel Syndrome", *Gastroenterology*, vol. 108, pp. 636-643 (1994).

Accarino, et al, "Attention And Distraction Colon Affects On Gut Perception", *Gastroenterology*, vol. 113, pp. 415-442 (1997).

Accarino, et al "Modification Of Small Bowel Mechanosensitivity By Intestinal Fat", *Gut*, vol. 48, pp. 690-695 (2001).

Accarino, et al, "Gut Perception In Humans Is Modulated By Interacting Gut Stimuli", *Am. J. Physiol. Gastrointestinal Liver Physiol.*, vol. 282, pp. G220-G225 (2002).

Bard® Minnesota Four Lumen Esophagogastric Tamponade Tube for the Control of Bleeding from Esophageal Varices (Instructions for Use), C. R. Bard, Inc., Covington, GA, USA (1998).

Baron, et al., "Acute Necrotizing Pancreatitis", *New England J. of Medicine*, vol. 340, No. 18, pp. 1412-1417 (1999).

U.S. Appl. No. 10/358,093, Beglinger et al., "Postprandial Control of Gallbladder Contraction and Exocrine Pancreatic Secretion in Man", Euro. J. of Clinical Investigation, pp. 827-834 (1992).

U.S. Appl. No. 10/358,093, Bell, et al., "The Interplay between Hydrogen Ions, Bicarbonate Ions and Osmolality in the Anterior Duodenuym Modulating Gastric Function in the Conscious Calf", *J. Physiol.*, pp. 331-341 (1981).

U.S. Appl. No. 10/358,093, Benini, "Gastric Emptying and Dyspeptic Symptoms in Patients with Gastroesophageal Reflux", Amer. J. of Gastroenterology, pp. 1351-1354 (1996).

U.S. Appl. No. 10/358,093, Benini, et al., "Omeprazole Causes Delay in Gastric Emptying of Digestible Meals", *Digestive Diseases and Sciences*, pp. 469-474 (1996).

U.S. Appl. No. 10/358,093, Berthoud et al., "Characterisitics of Gastric and Pancreatic Responses to Vagal Stimulation with Varied Frequencies: Evidence for Different Fiber Calibers?", *J. Auto. Nervous Sys.*, pp. 77-84 (1987).

Biron, et al., "Clinical Experience with Biliopancreatic Bypass and Gastrectomy or Selective Vagotomy for Morbid Obesity", *Canadian J. of Surg.*, vol. 29, vol. 6, pp. 408-410 (1986).

U.S. Appl. No. 10/358,093, Bourde, et al., "Vagal Stimulation: II. Its Effect on Pancreatic Secretion in Conscious Dogs", *Annals of Surgery*, pp. 357-364 (1970).

"Bravo™ pH Monitoring System Catheter-Free pH Testing", document No. UC 200300235 EN N15344, Medtronic, Inc., Minneapolis, Minnesota, USA (2002).

Burneo, et al., "Weight Loss Associated With Vagus Nerve Stimulation", *Neurology*, vol. 59, pp. 463-464 (Aug. (1 of 2) 2002).

Chatzicostas, et al., "Balthazar computed tomography severity index is superior to Ranson criteria and Apache II and II scoring systems in predicting acute pancreatitis outcome", *J. Clinical Gastroenterology*, 36(3), pp. 253-260 (2003).

U.S. Appl. No. 10/358,093, Chey et al., "Neural Hormonal Regulation of Exocrine Pancreatic Secretion", Pancreatology, pp. 320-335 (2001).

U.S. Appl. No. 10/358,093, Chey, "Regulation of Pancreatic Exocrine Secretion", Int'l J. of Pancreatology, pp. 7-20 (1991).

Cigaina, "Gastric Pacing As Therapy For Morbid Obesity", *Obesity Surgery*, vol. 12, Supplement, pp. 12S-16S (2002).

Coffin, et al, "Somatic Stimulation Reduces Perception Of Gut Distention In Humans", *Gastroenterology*, vol. 107, pp. 1636-1642 (1994).

Cyberonics, Inc 2001 Annual Report, pp. 1, 5-7 and 16 (2001).

Cyberonics, Inc. 2003 Form 10-K to Securities and Exchange Commission, pp. 1 and 10 as printed on May 23, 2006 from http://www.secinfo.com/dsvRu.23yb.htm.

D'Argent, "Gastric Electrical Stimulation: Preliminary Results", *Obesity Surgery*, vol. 12, Supplement, pp. 21S-25S (2002).

U.S. Appl. No. 10/674,330, DeVault KR, et al., "Updated Guidelines for the Diagnosis and Treatment of Gastroesophageal Reflux Disease", *Am J Gastroenterol*, (1999);94:1434-1442.

U.S. Appl. No. 10/358,093, Estevão-Costa et al., "Delayed Gastric Emptying and Gastroesophageal Reflux: A Pathophysiologic Relationship", J. of Pediatric Gastroenterology and Nutrition, pp. 471-474 (2001).

Faris, et al., "Effect of Decreasing Afferent Vagal Activity with Ondansetron on Symptoms of Bulimia Nervosa: a Randomized, Double-Blind Trial", *The Lancet*, pp. 792-797 (2000).

George, et al., "Vagus Nerve Stimulation Therapy", *Neurology*, vol. 59 (Suppl 4) pp. S56-S61 (2002).

Gleysteen, et al., "Reversible Truncal Vagotomy in Conscious Dogs", *Gastroenterology*, vol. 86, pp. 578-583 (1983).

Gortz, et al., "Truncal Vagotomy Reduces Food and Liquid Intake in Man", *Physiology & Behavior*, vol. 48, pp. 779-781 (1990).

Gray, *Anatomy of the Human Body*, 13th Ed., C. Clemente, Editor, (Lea & Febiger, Philadelphia, PA USA, Publisher) (1985) title pages and p. 69, 70 and 1186.

U.S. Appl. No. 10/358,093, Grossi, et al., "Swallows, Oesophageal and Gastric Motility in Normal Subjects and in Patients with Gatro-Oesophageal Reflux Disease: a 24-H pH-Manometric Study", Neurogatroenterology and Motility, pp. 115-121 (1998).

Holst et al., "Nervous Control of Pancreatic Exocrine Secretion in Pigs", *Acta Physiol. Scand.*, vol. 105, pp. 33-51 (1979).

U.S. Appl. No. 10/358,093, Hunt, "The Relationship Between The Control Of pH And Healing And Symptom Relief In Gastro-Oesophageal Reflux Disease", *Ailment Pharmacol Ther.*, 9 (Suppl. 1) pp. 3-7 (1995).

ICD-10, "Classification of Mental and Behavioural Disorders", World Health Organization (1992), 2 pages, printed from http://www.mental-health-matters.com/disorders/dis_details.

Kaiser, "Gallstone Ileus", *New England J. of Medicine*, vol. 336, No. 12, pp. 879-880 (1997) (correspondence).

U.S. Appl. No. 10/358,093, Kaminski et al., "The Effect of Electrical Vagal Stimulation on Canine Pancreatic Exocrine Function", Surgery, pp. 545-552 (1975).

Koren et al., "Vagus Nerve Stimulation Does Not Lead To Significant Changes In Body Weight In Patients With Epilepsy", *Epilepsy & Behavior*, vol. 8, pp. 246-249 (2005).

Kosel, et al., "Beyond the Treatment of Epilepsy: New Applications of Vagus Nerve Stimulation in Psychiatry", *CNS Spectrums*, vol. 8, No. 7, pp. 515-521 (Jul. 2003).

Kral, "Vagotomy for Treatment of Severe Obesity", *The Lancet*, pp. 307-308 (1978).

Kral, "Vagotomy as a Treatment for Morbid Obesity", *Surg. Clinics of N. Amer.*, vol. 59, No. 6, pp. 1131-1138 (1979).

Kral, et al., "Gastroplasty for Obesity: Long-Term Weight Loss Improved by Vagotomy", *World J. Surg.*, vol. 17, pp. 75-79 (1993).

U.S. Appl. No. 10/358,093, Long, M.S. editor, Chapter 3, "The Stomach", Gastrointestinal System, 2nd Ed., Mosby Publisher, London (2002).

U.S. Appl. No. 10/358,093, Long, M.S. editor, Chapter 4, "The Liver and Biliary Tract", Gastrointestinal System, 2nd Ed., Mosby Publisher, London (2002).

U.S. Appl. No. 10/358,093, Mabayo, et al., "Inhibition of Food Passage by Osmeprazole in the Chicken", European J. of Pharmacology, pp. 161-165 (1995).

Martin-Portugues, et al., "Histopathologic Features of the Vagus Nerve After Electrical Stimulation in Swine", *Histol Histopathol*, vol. 20, pp. 851-856 (2005).

"Medical Care for Obese Patients", U.S. Department of Health and Human Services, National Institute of Diabetes and Digestive and Kidney Disease, pp. 1-6, NIH Publication No. 03-5335, Feb. 2003.

Medical Encyclopedia: Anorexia Nervosa, U.S. National Library of Medicine and National Institutes of Health, pp. 1-3 (Jun. 22, 2004) printed from http://www.nlm.nih.gov/medlineplus/print/ency/article/000362.htm, Jun. 6, 2006.

Netter, "Atlas of Human Anatomy", 3rd Ed., Plate 120, (Icon Learning Systems, New Jersey) (2003).

Norton, et al., "Optimizing Outcomes in Acute Pancreatitis", *Drugs*, 61(11), pp. 1581-1591 (2001).

O'Brien, P. et al., "The Laparascopic Adjustable Gastric Band (Lap-Band®): A Prospective Study of Medium-Term Effects on Weight, Health and Quality of Life," *Obesity Surgery*, vol. 12, pp. 652-660 (2002).

"Obesity and Technology: Can the stomach be fooled", Reuters (Apr. 26, 2006), 3 pages, http://news.yahoo.com/s/nm/20060426/us_nm/bizfeature_obesity_technology_de&printer as printed on May 23, 2006.

U.S. Appl. No. 10/358,093, Owyang, "Negative Feedback Control of Exocrine Pancrfeatic Secretion: Role of Cholecystokinin and Cholinergic Pathway", Symposium: Physiology of Cholecystokinin, American Institute of Nutrition, pp. 1321S-1326S (1994).

Peeters, et al., "Obesity in Adulthood and Its Consequences for Life Expectancy: A Life Table Analysis", *Annals of Internal Medicine*, vol. 138, No. 1, pp. 24-32 (2003).

U.S. Appl. No. 10/358,093, Rasmussen, et al., "A Double-Blind Placebo-Controlled Study on the Effects of Omeprazole on Gut Hormone Secretion and Gastric Emptying Rate", Scand. J. Gastroenterol, pp. 900-905 (1997).

U.S. Appl. No. 10/358,093, Rösch et al., "Frequency-Dependent Secretion of Pancreatic Amylase, Lipase, Trypsin, and Chymotrypsin During Vagal Stimulation in Rats", *Pancreas*, pp. 499-506 (1990).

Roslin, et al., "Vagus Nerve Stimulation in the Treatment of Morbid Obesity", Ch. 6 to *Vagus Nerve Stimulation*, 2nd Ed., pp. 113-121 (Schlachter et al. ed., Martin Dunitz), 2003.

Roslin et al., "The Use Of Electrical Stimulation Of The Vagus Nerve To Treat Morbid Obesity", *Epilepsy & Behavior*, vol. 2, S11-S16 (2001) at p. S13.

U.S. Appl. No. 10/358,093, Schapiro, et al., "Neurohypophyseal Regulation of the Exocrine Pancreas", *Amer. J. of Gastroenterology*, pp. 587-591 (1979).

Shikora, "'What are the Yanks Doing' The U.S. Experience with Implantable Gastric Stimulation (IGS) for the Treatment of Obesity—Update on the Ongoing Clinical Trials", *Obesity Surgery*, vol. 14, Supplement, S40-S48 (2004).

Smith, et al., "Truncal Vagotomy in Hypothalamic Obesity", *The Lancet*, pp. 1330-1331 (1983).

Soran, et al., "Outcome and quality of life of patients with acute pancreatitis requiring intensive care", *J. Surg. Res.*, 91(1), pp. 89-94 (2000).

Steer et al., "Chronic Pancreatitis", *New England J. of Medicine*, pp. 1482-1490 (1995).

Steinbrook, R., "Surgery for Severe Obesity", *New England J. Med.*, vol. 350, pp. 1075-1079 (2004).

Steinbrook, "An Opioid Antagonist For Postoperative Ileus", *New England J. of Medicine*, vol. 345, No. 13, pp. 988-989 (2001) (Editorial).

Taguchi, et al., "Selective Postoperative Inhibition of Gastrointestinal Opioid Receptors", *New England J. of Medicine*, vol. 345, No. 13, pp. 935-940 (2001).

U.S. Appl. No. 10/674,330, Talley et al., "Rome II: A Multinational Consensus Document on Gastrointestinal Disorders—Functional Gastroduodenal Disorders" *Gut*, vol. 45 (Suppl II), pp. 137-1142 (1999).

U.S. Appl. No. 10/358,093, Tiscornia et al., "Neural Control of the Exocrine Pancreas: An Analysis of the Cholinergic, Adrenergic, and Peptidergic Pathways and Their Positive and Negative Components 1: Neural Mechanisms", *Mount Sinai J. of Medicine*, pp. 366-383 (1987).

Tzu-Ming, et al., "Long-Term Results of Duodenectomy with Highly Selective Vagotomy in the Treatment of complicated Duodenal Ulcers", *Amer. J. of Surg.*, vol. 181, pp. 372-376 (2001).

Yoshinaga, et al., "Cholecystokinin Acts as an Essential Factor in the Exacerbation of Pancreatic Bile Duct Ligation-Induced Rat Pancreatitis Model Under Non-Fasting Condition", *Japanese J. Pharmacol*, vol. 84, pp. 44-50 (2000).

Zapater, et al., "Do Muscarinic Receptors Play a Role in Acute Pancreatitis?", *Clin. Drug Invest.*, 20(6), pp. 401-408 (2000).

Balaji, et al., "A Safe and Noninvasive Test for Vagal Integrity Revisited", *Archive Surgery*, vol. 137, pp. 954-959 (2002).

Boss, et al., Laparoscopic Truncal Vagotomy for Severe Obesity: Six Month Experience in 10 Patients from a Prospective, Two-Center Study, Proceedings of the 24th Annual Meeting, American Society for Metabolic & Bariatric Surgery, Plenary Session Abstracts, (Abstract No. 44) (Jun. 2007) (reprinted from http://www.asbs.org/archive/abstracts/plenary_edited_2007.pdf).

Davidson, et al., "Long-Term Effects of Botulinum Toxin Injections in Spasmodic Dysphonia", *Ann. Otol. Rhinol. Laryngol.*, vol. 105, pp. 34-42 (1996).

Görtz, et al., "A Five- to Eight-Year Follow-up Study of Truncal Vagotomy as a Treatment for Morbid Obesity", Proceedings of the Third Annual Meeting, American Society for Bariatric Surgery, p. 145 (1986) (Abstract).

Gui, et al., "Botulinum Toxin Injected in the Gastric Wall Reduces Body Weight and Food Intake in Rats", *Aliment Pharmacol Ther.*, vol. 14, pp. 829-834 (2000).

Sautter, et al., "Transient Paralysis of the Bladder due to Wound Botulism", *Eur. Urol.*, vol. 39, pp. 610-612 (2001).

Illustrated Stedman's Medical Dictionary, 24th Edition, Williams & Wilkins, Baltimore, MD, USA, Publisher, title pages and p. 3 (1982).

Taylor, et al., "Effects of Pancreatic Polypeptide, Cacrulein, and Bombesin on Satiety in Obese Mice", *American Journal of Physiology*, 248:G277-G280 (1985).

Camilleri et al., "Determinants of Response to a Prokinetic Agent in Neuropathic Chronic Intestinal Motility Disorder", *American Gastroenterological Association*, vol. 106, No. 4, pp. 916-923 (1994).

Greydanus et al., "Neurohormonal Factors in Functional Dyspepsia: Insights on Pathophysiological Mechanisms", *American Gastroenterological Association*, vol. 100, No. 5, pp. 1311-1318 (1991).

Hassall et al., "Mechanisms of Gastroesophageal Reflux and Gastroesophageal Reflux Disease", *Journal of Pediatric Gastroenterology and Nutrition*, 35:119-136 (Aug. 2002).

Koch et al., "Can Plasma Human Pancreatic Polypeptide Be Used to Detect Diseases of the Exocrine Pancreas?", *Mayo Clinic Proc.*, Apr. 1985, vol. 60, pp. 259-265.

Layer et al., "Human pancreatic secretion during phase II antral motility of the interdigestive cycle", *American Physiological Society*, 88 G249-G253 (1988).

Mokdad et al., "Prevalence of Obesity, Diabetes, and Obesity-Related Health Risk Factors, 2001", *JAMA*, vol. 289, No. 1 (Jan. 1, 2003).

Office Action mailed Apr. 21, 2008 in U.S. Appl. No. 11/040,767.

Partial International Search Report mailed Aug. 28, 2008.

\* cited by examiner

Low Vagal and Enteric Tone Before Pacing

Pacing Without Block

Implantable System
*Beta Medical - Vagus Nerve Stimulation System*

Pacing With Proximal Block

Pacing With Proximal and Distal Blocks

Blocking without Stimulation

VAGAL DOWN-REGULATION OBESITY TREATMENT

I. CROSS-REFERENCE TO RELATED APPLICATION

The present application is a continuation-in-part application of U.S. patent application Ser. No. 10/358,093 filed Feb. 3, 2003 and entitled "Method and Apparatus for Treatment of Gastroesophageal Disease (GERD)" (now abandoned). The present application discloses and claims subject matter disclosed in the following commonly assigned and U.S. patent applications filed on the same date as the present application and in the name of the same inventors: U.S. patent application Ser. No. 10/675,818, entitled "Enteric Rhythm Management" and U.S. patent application Ser. No. 10/674,324, entitled "Nerve Stimulation And Conduction Block Therapy".

II. BACKGROUND OF THE INVENTION

1. Field of the Invention

This invention pertains to treatments of disorders associated, at least in part, with neural activity. These may include, without limitation, gastrointestinal, pancreo-biliary, cardio-respiratory and central nervous system disorders (including neurological and psychiatric, psychological and panic disorders). More particularly, this invention pertains to treatment of such disorders through management of neural impulse stimulation and blocking.

2. Description of the Prior Art

A. Functional Gastrointestinal Disorders (FGIDs)

Functional Gastrointestinal Disorders (FGIDs) are a diagnostic grouping having diagnostic criteria based on symptomatology, because the pathophysiology of these diseases is multifactorial with some pathophysiologic mechanisms in common. FGIDs are thought to be due to altered autonomic nervous system balance and to be pathophysiological combinations of: (1) abnormal GI motility; (2) visceral hypersensitivity; and, (3) brain-gut interactions. Tougas, "The Autonomic Nervous System in Functional Bowel Disorders", *Gut*, Vol. 47 (Suppl IV), pp. iv78-iv80 (2000) and Drossman, "Rome II: A Multinational Consensus Document on Gastrointestinal Disorders—The Functional Gastrointestinal Disorders and the Rome II Process", *Gut*, Vol. 45 (Suppl II):II1-II5 (1999). The FGIDs of interest to the present invention are functional dyspepsia (dysmotility-like) and irritable bowel syndrome (IBS).

1. Functional Dyspepsia (Dysmotility-like)

Functional dyspepsia (dysmotility-like), is diagnosed when a patient's symptoms, in the absence of other organic disease likely to explain the symptoms, include persistent or recurrent pain or discomfort centered in the upper abdomen that may be accompanied by upper abdominal fullness, early satiety, bloating or nausea. Talley et al., "Rome II: A Multinational Consensus Document on Gastrointestinal Disorders—Functional Gastroduodenal Disorders" *Gut*, Vol. 45 (Suppl II), pp. I37-II42 (1999).

A spectrum of dysmotilities has been documented in patients with functional dyspepsia. These include delayed gastric emptying of solids and liquids, reduced vagal tone, gastric dysrhythmias and impaired gastric accommodation. Furthermore, some studies have found good correlation between symptoms and indices of dysmotility, while others have not. Stanghellini V, et al., "Delayed Gastric Emptying of Solids in Patients with Functional Dyspepsia", *Gastroenterol*, (1996) 110:1036-1042. Undeland K A, et al., "Wide Gastric Antrum and Low Vagal Tone in Patients with Diabetes Mellitus Type 1 Compared to Patients with Functional Dyspepsia and Healthy Individuals", *Dig Dis Sci*, (1996) 41:9-16. Tack J, et al., "Role of Impaired Gastric Accommodation to a Meal in Functional Dyspepsia", *Gastroenterol*, (1998) 115: 1346-1352. Wilmer A, et al., "Ambulatory Gastrojejunal Manometry in Severe Motility-like Dyspepsia: Lack of Correlation between Dysmotility, Symptoms and Gastric Emptying", *Gut*, (1998) 42:235-242. Tack J, et al., "Symptom Pattern and Gastric Emptying Rate Assessed by the Octanoic Acid Breath Test in Functional Dyspepsia" [abstract]. *Gastroenterol*, (1998) 114:A301. Cuomo R, et al., "Functional Dyspepsia Symptoms, Gastric Emptying and Satiety Provocation Test: Analysis of Relationships", *Scand J Gastroenterol*, (2001) 36:1030-1036. Sarnelli G, et al., "Symptoms Associated with Impaired Gastric Emptying of Solids and Liquids in Functional Dyspepsia", *Am J Gastroenterol*, (2003) 98:783-788.

2. Irritable Bowel Syndrome (IBS)

The second FGID of interest, IBS, is diagnosed when a patient's symptoms include persistent abdominal pain or discomfort, in the absence of other explanatory organic disease, along with at least two of the following: relief of pain with defecation, onset of symptoms associated with a change in frequency of stools and/or onset of symptoms associated with a change in appearance/form of stools. Thompson W G, et al., "Rome II: A Multinational Consensus Document on Gastrointestinal Disorders —Functional Bowel Disorders and Functional Abdominal Pain", *Gut*, (1999);45(Suppl II):II43-II47.

In addition to colonic dysmotility, a number of other GI motility abnormalities have been identified, including delayed gastric emptying, gastroparesis, and small intestine motility abnormalities. Vassallo M J, et al., "Colonic Tone and Motility in Patients with Irritable Bowel Syndrome", *Mayo Clin Proc*, (1992);67:725-731. Van Wijk H J, et al., "Gastric Emptying and Dyspeptic Symptoms in the Irritable Bowel Syndrome", *Scand J Gastroenterol*, (1992);27:99-102. Evans P R, et al., "Gastroparesis and Small Bowel Dysmotility in Irritable Bowel Syndrome", *Dig Dis Sci* (1997);42:2087-2093. Cann P A, et al. "Irritable Bowel Syndrome: Relationship of Disorders in the Transit of a Single Solid Meal to Symptoms Patterns", *Gut*, (1983);24:405-411. Kellow J E, et al., "Dysmotility of the Small Intestine in Irritable Bowel Syndrome", *Gut*, (1988);29:1236-1243. Evans P R, et al., "Jejunal Sensorimotor Dysfunction in Irritable Bowel Syndrome: Clinical and Psychosocial Features", Gastroenterol, (1996);110:393-404. Schmidt T, et al., "Ambulatory 24-Hour Jejunal Motility in Diarrhea-Predominant Irritable Bowel Syndrome", *J Gastroenterol*, (1996);31:581-589. Simren M, et al., "Abnormal Propagation Pattern of Duodenal Pressure Waves in the Irritable Bowel Syndrome (IBS)", *Dig Dis Sci*, (2000);45:2151-2161.

A related finding is that patients with constipation-predominant IBS have evidence of decreased vagal tone, while diarrhea-predominant IBS is associated with evidence of increased sympathetic activity. Aggarwal A, et al., "Predominant Symptoms in Irritable Bowel Syndrome Correlate with Specific Autonomic Nervous system Abnormalities", *Gastroenterol*, (1994); 106:945-950.

There is no cure for IBS. Treatments include supportive palliative care (antidiarrheals, dietary modification and counseling).

A recently approved drug to treat selected patients with FGIDs is tegaserod maleate sold under the tradename "Zelnorme®" by Novartis Pharmaceuticals Corp., East Hanover, N.J., USA. The product literature on Zelnorm recognizes the enteric nervous system is a key element in treating IBS. The literature suggests Zelnorm® acts to enhance basal motor activity and to normalize impaired motility. Novartis product description, Zelnorm®, July 2002 (T2002-19). Zelnorm's approved use is limited to females with constipation-related IBS. It is for short-term use only.

B. Gastroparesis

The third disease indication discussed here, gastroparesis (or delayed gastric emptying) is associated with upper GI symptoms such as nausea, vomiting fullness, bloating and early satiety. Gastroparesis can be caused by many underlying conditions. The most important, because of chronicity and prevalence, are diabetes, idiopathic and post-surgical. Hornbuckle K, et al. "The Diagnosis and Work-Up of the Patient with Gastroparesis", *J Clin Gastroenterol*, (2000);30: 117-124. GI dysmotility in the form of delayed gastric emptying is, by definition, present in these patients.

In patients with Type 1 diabetes mellitus and delayed gastric emptying, there appears to be a relationship between delayed gastric emptying and low vagal tone. Merio R, et al., "Slow Gastric Emptying in Type 1 Diabetes: Relation to Autonomic and Peripheral Neuropathy, Blood Glucose, and Glycemic Control", *Diabetes Care*, (1997);20:419-423. A related finding is that patients with Type 1 diabetes have low vagal tone in association with increased gastric antral size, possibly contributing to the dysmotility-associated symptoms seen in these patients. Undeland K A, et al., "Wide Gastric Antrum and Low Vagal Tone in Patients with Diabetes Mellitus Type 1 Compared to Patients with Functional Dyspepsia and Healthy Individuals", *Dig Dis Sci*, (1996);41:9-16.

The current treatments for gastroparesis are far from satisfactory. They include supportive care, such as dietary modification, prokinetic drugs, and; when required, interventions such as intravenous fluids and placement of a nasogastric tube may be needed.

C. Gastroesophageal Reflux Disease (GERD)

The fourth indication, GERD, can be associated with a wide spectrum of symptoms, including dyspepsia, reflux of gastric contents into the mouth, dysphagia, persistent cough, refractory hyperreactive airway disease and even chronic serous otitis media. Sontag S J, et al., "Asthmatics with Gastroesophageal Reflux: Long Term Results of a Randomized Trial of Medical and Surgical Antireflux Therapies", *Am J Gastroenterol*, (2003);98:987-999. Poelmans J, et al., "Prospective Study on the Incidence of Chronic Ear Complaints Related to Gastroesophageal Reflux and on the Outcome of Antireflux Therapy", *Ann Otol Rhinol Laryngol*, (2002); 111: 933-938.

GERD is considered to be a chronic condition for which long-term medical therapy and/or surgical therapy is often deemed necessary, in significant part because esophageal adenocarcinoma is sometimes a consequence of GERD. DeVault K R, et al., "Updated Guidelines for the Diagnosis and Treatment of Gastroesophageal Reflux Disease", *Am J Gastroenterol*, (1999);94:1434-1442. Lagergren J, et al., "Symptomatic Gastroesophageal Reflux as a Risk Factor for Esophageal Adenocarcinoma", *New Engl J Med*, (1999);340: 825-831.

The underlying pathophysiological mechanisms in GERD are considered to be transient lower esophageal relaxations (TLESRs) in the presence of either an inadequate pressure gradient between the stomach and the esophagus across the lower esophageal sphincter and/or low amplitude esophageal activity at times when gastric contents do reflux into the esophagus. In addition, gastric distention is thought to be associated with an increase in TLESRs. Mittal R K, et al., "Mechanism of Disease: The Esophagogastric Junction", *New Engl J Med*, (1997);336:924-932. Scheffer R C, et al., "Elicitation of Transient Lower Oesophageal Sphincter Relaxations in Response to Gastric Distension", *Neurogastroenterol Motil*, (2002);14:647-655.

GERD is generally considered to be the result of a motility disorder which permits the abnormal and prolonged exposure of the esophageal lumen to acidic gastric contents. Hunt, "The Relationship Between The Control Of pH And Healing And Symptom Relief In Gastro-Oesophageal Reflux Disease", *Ailment Pharmacol Ther.*, 9 (Suppl. 1) pp. 3-7 (1995). Many factors are believed to contribute to the onset of GERD. These include transient lower esophageal sphincter relaxations (as previously described), decreased LES resting tone, delayed stomach emptying and an ineffective esophageal clearance.

Certain drugs have had some effectiveness at controlling GERD but fail to treat underlying causes of the disease. Examples of such drugs are $H_2$-receptor antagonists (which control gastric acid secretion in the basal state) and proton pump inhibitors (which control meal-stimulated acid secretion). Hunt, id. Both classes of drugs can raise intragastric pH to or about 4 for varying durations. Hunt, supra.

Surgery treatments are also employed for the treatment of GERD and include techniques for bulking the lower esophageal sphincter such as fundoplication and techniques described in U.S. Pat. No. 6,098,629 Johnson et al, Aug. 8, 2000. Other surgical techniques include placement of pacemakers for stimulating muscle contractions in the esophageal sphincter, the stomach muscles or in the pyloric valve. U.S. Pat. No. 6,104,955 to Bourgeois, U.S. Pat. No. 5,861,014 to Familoni.

A summary of GERD treatments can be found in DeVault, et al., "Updated Guidelines for the Diagnosis and Treatment of Gastroesophageal Reflux Disease", Amer. J. of Gastroenterology, Vol. 94, No. 6, pp. 1434-1442 (1999).

Notwithstanding multiple attempts at various types of treatment, GERD continues to be a serious disease proving to be difficult to treat by any of the foregoing prior art techniques. In view of the foregoing and notwithstanding various efforts exemplified in the prior art, there remains a need for an effective treatment for GERD. It is an object of the present invention to provide a novel treatment and novel apparatus for the treatment of GERD.

D. Electrical Stimulation to Treat GI Disorders

Treatment of gastrointestinal diseases through nerve stimulation have been suggested. For example, U.S. Past. No. 6,238,423 to Bardy dated May 29, 2001 describes a constipation treatment involving electrical stimulation of the muscles or related nerves of the gut. U.S. Pat. No. 6,571,127 to Ben-Haim et al. dated May 27, 2003 describes increasing motility by applying an electrical field to the GI tract. U.S. Pat. No. 5,540,730 to Terry, Jr. et al., dated Jul. 30, 1996 describes a motility treatment involving vagal stimulation to alter GI contractions in response to a sense condition indicative of need for treatment. The '730 patent also uses a definition of dysmotility more restrictive than in the present application. In the '730 patent, dysmotility is described as hyper- or hypo-contractility. In the present application, dysmotility is a broader concept to refer to all abnormalities of gastric emptying or bowel transfer regardless of cause. U.S. Pat. No. 6,610,713 to Tracey dated Aug. 26, 2003 describes inhibiting release of a proinflammatory cytokine by treating a cell with a cholinergic agonist by stimulating efferent vagus nerve activity to inhibit the inflammatory cytokine cascade.

A substantial body of literature is developed on nerve stimulation. For example, in Dapoigny et al., "Vagal influence on colonic motor activity in conscious nonhuman primates", *Am. J. Physiol.*, 262: G231-G236 (1992), vagal influence on colonic motor activity was investigated in conscious monkeys. To block antidromic interference, the vagus was blocked via vagal cooling and a vagal stimulation electrode was implanted distal to the vagal block. It was noted that vagal efferent stimulation increased contractile frequency and that the vagus has either a direct or indirect influence on fasting and fed colonic motor activity throughout the colon, and that a non-adrenergic, noncholinergic inhibitory pathway is under vagal control.

Colonic and gastric stimulation are also described in a number of articles associated with M. P. Mintchev. These include: Mintchev, et al., "Electrogastrographic impact of multi-site functional gastric electrical stimulation", *J. of Medical Eng. & Tech.*, Vol. 23, No. 1 pp. 5-9 (1999); Rashev, et al., "Three-dimensional static parametric modeling of phasic colonic contractions for the purpose of microprocessor-controlled functional stimulation", *J. of Medical Eng. & Tech.*, Vol. 25, No. 3 pp. 85-96 (2001); Lin et al., "Hardware-software co-design of portable functional gastrointestinal stimulator system", *J. of Medical Eng. & Tech.*, Vol. 27, No. 4 pp. 164-177 (2003); Amaris et al., "Microprocessor controlled movement of solid colonic content using sequential neural electrical stimulation", *Gut*, 50: pp 475-479 (2002) and Rashev et al., "Microprocessor-Controlled Colonic Peristalsis", *Digestive Diseases and Sciences*, Vol. 47, No. 5, pp. 1034-1048 (2002).

The foregoing references describe nerve stimulation to stimulate muscular contraction in the GI tract. As will be more fully discussed, the present invention utilizes vagal stimulation to improve vagal tone (similar in concept to improving cardiac electrical tone through cardiac pacing) and/or to treat GI disorders by altering the nature of duodenum contents by stimulation pancreatic and biliary output. The invention is also applicable to treating other diseases such as neuropsychiatric disorders.

Vagal tone has been shown to be associated with dyspepsia. Hjelland, et al., "Vagal tone and meal-induced abdominal symptoms in healthy subjects", *Digestion*, 65: 172-176 (2002). Also, Hausken, et al., "Low Vagal Tone and Antral Dysmotility in Patients with Functional Dyspepsia", *Psychosomatic Medicine*, 55: 12-22 (1993). Also, decreased vagal tone has been associated with irritable bowel syndrome. Heitkemper, et al., "Evidence for Automatic Nervous System Imbalance in Women with Irritable Bowel Syndrome", *Digestive Diseases and Sciences*, Vol. 43, No. 9, pp. 2093-2098 (1998).

Also, as will be discussed, the present invention includes, in several embodiments, a blocking of a nerve (such as the vagal nerve) to avoid antidromic influences during stimulation. Cryogenic nerve blocking of the vagus is described in Dapoigny et al., "Vagal influence on colonic motor activity in conscious nonhuman primates", *Am. J. Physiol.*, 262: G231-G236 (1992). Electrically induced nerve blocking is described in Van Den Honert, et al., "Generation of Unidirectionally Propagated Action Potentials in a Peripheral Nerve by Brief Stimuli", *Science*, Vol. 206, pp. 1311-1312. An electrical nerve block is described in Solomonow, et al., "Control of Muscle Contractile Force through Indirect High-Frequency Stimulation", *Am. J. of Physical Medicine*, Vol. 62, No. 2, pp. 71-82 (1983) and Petrofsky, et al., "Impact of Recruitment Order on Electrode Design for Neural Prosthetics of Skeletal Muscle", *Am. J. of Physical Medicine*, Vol. 60, No.5, pp. 243-253 (1981). A neural prosthesis with an electrical nerve block is also described in U.S. Patent Application Publication No. US 2002/0055779 A1 to Andrews published May 9, 2002. A cryogenic vagal block and resulting effect on gastric emptying are described in Paterson C A, et al., "Determinants of Occurrence and Volume of Transpyloric Flow During Gastric Emptying of Liquids in Dogs: Importance of Vagal Input", *Dig Dis Sci*, (2000);45:1509-1516.

III. SUMMARY OF THE INVENTION

According to a preferred embodiment of the present invention, a method and apparatus are disclosed for treating at least one of a plurality of gastrointestinal disorders of a patient characterized at least in part by an altered autonomic balance or altered motility. The method includes electrically stimulating an enteric nervous system of the patient to enhance a functional tone of the enteric nervous system.

Enteric rhythm management (ERM) treats GI diseases in which dysmotility is thought to play a major role. This therapy is based on the physiological actions of pancreatic exocrine secretion and bile on the composition (osmolality and pH) and the digestion (enzymatic activity and, in the case of fats, emulsification) of intraduodenal chyme, thereby presenting a novel approach to regulating the motility of the GI tract and, in particular, gastric emptying and the digestion and propulsion of chyme through the duodenum and into the jejunum and ileum.

ERM as a therapy for GI diseases involving dysmotility is based on the following: (1) pacing the delivery of pancreatic exocrine secretion and bile can be used to either up- or down-regulate at least two aspects of GI motility-gastric emptying and small bowel transit—by modulating the osmolality, the pH and the digestion, including emulsification as needed, of intra-duodenal chyme; (2) pacing the efferent activity of the intra-abdominal vagus nerve as needed while blocking afferent activity of that same nerve as needed can be used to treat GI dysmotility in patients with either increased or decreased vagal tone as a component of their disease; and, (3) treating GI dysmotility disorders can and often does require flexibility in adjusting treatment algorithms based on symptomatic response because of inter-patient differences with a diagnostic group and because of intra-patient variability over time.

The goals of enteric rhythm management in gastroparesis are: 1) to regulate the composition and digestion of duodenal chyme and, by so doing, to facilitate gastric emptying through the modulatory effect of duodenal chemo- and mechanoreceptors on the pylorus and 2) to up-regulate or down-regulate vagal tone to optimize gastricintestinal motility and symptom relief.

In patient with GERD, ERM utilizing a physiologic enteric pacing device will, as described earlier, allow pacing of the delivery of pancreatic exocrine secretion and bile, thereby initiating pyloric relaxation, gastric emptying and consequent reduction in gastric distention, leading to a decrease in the underlying mechanism of GERD, that is, TLESRs.

Kellow J E, et al., "Rome II: A Multinational Consensus Document on Gastrointestinal Disorders—Principles of Applied Neurogastroenterology: Physiology/Motility-Sensation", *Gut*, (1999);45(Suppl II):II17-II24. Paterson C A, et al., "Determinants of Occurrence and Volume of Transpyloric Flow During Gastric Emptying of Liquids in Dogs: Importance of Vagal Input", *Dig Dis Sci*, (2000);45:1509-1516. Tougas G, "The Autonomic Nervous System in Functional Bowel Disorders", *Gut*, (2000);47(Suppl IV):iv78-iv80. Guyton A C, et al., "Propulsion and Mixing of Food in the Alimentary Tract", Textbook of Medical Physiology, $10^{th}$ ed.

Philadelphia: W. B. Saunders and Company, 200:728-737. Guyton A C, et al., "Secretory Functions of the Alimentary Tract", Textbook of Medical Physiology, 10$^{th}$ ed. Philadelphia: W. B. Saunders and Company, 200:738-753. Schwartz M P, et al., "Human Duodenal Motor Activity in Response to Acid and Different Nutrients", *Dig Dis Sci*, (2001);46:1472-1481. Schwartz M P, et al., "Chemospecific Alterations in Duodenal Perception and Motor Response in Functional Dyspepsia", *Am J Gastroenterol*, (2001);96:2596-2602.

ERM involves pacing and thereby regulating the timing and the volume of pancreatic exocrine secretion and bile delivered to the intraluminal contents of the duodenum. In one embodiment, this is accomplished with a small, laparoscopically implantable and programmable medical device called a physiologic enteric pacing device. Three leads are positioned intra-abdominally and then connected to a subcutaneous, programmable pulse generator. A pacing lead may be placed on the anterior vagal trunk and another pacing lead may be placed on the posterior vagal trunk. One or more intra-abdominal electrode, i.e. blocking electrodes, may be placed on the vagus nerve proximal to the pacing leads.

An additional embodiment of the present invention pertains to treating at least one of a plurality of gastrointestinal disorders of a patient by electrically stimulating a vagus nerve of the patient at a stimulation site proximal to at least one site of vagal innervation of a gastrointestinal organ. The electrical stimulation includes applying a stimulation signal at the stimulation site. A proximal electrical blocking signal is applied to the vagus nerve at a proximal blocking site proximal to the stimulation site. The proximal blocking signal is selected to at least partially block nerve impulses proximal to the proximal blocking site.

The invention further includes a treatment apparatus having a stimulation electrode adapted for placement on a nerve of a patient at a stimulation site and a stimulation signal generator for generating a stimulation signal at the stimulation electrode and selected to electrically stimulate a nerve to induce bi-directional propagation of nervous impulses in a stimulated nerve. The apparatus includes a blocking member for placement on the nerve at a blocking site and creating localized conditions at the blocking site that at least partially diminish transmission of nerve impulses past the blocking site.

A still further embodiment of the present invention includes a method for treating at least one of a plurality of disorders of a patient where the disorders are associated with a gastrointestinal tract of a patient where the disorders are characterized at least in part by hyper-tonal vagal activity innervating at least one of a plurality of alimentary tract organs of the patient at an innervation site. The method includes applying a neural conduction block to a vagus nerve of the patient at a blocking site proximal to the innervation site. The neural conduction block is selected to at least partially block nerve impulses on the vagus nerve distal to the blocking site.

A yet further embodiment pertains to a treatment apparatus having an electrically controllable neural conduction electrode adapted to be placed on a vagus nerve of a patient at a blocking site proximal to an innervation site. A blocking signal generator generates a blocking signal selected to at least partially block nerve impulses on the vagus nerve distal to the blocking site.

A still additional embodiment of the present invention includes a method for treating at least one of a plurality of disorders of a patient by electrically stimulating a vagus nerve at a stimulation site with a stimulation signal selected to have a therapeutic effect on a target organ. An electrical blocking signal is applied to the vagus nerve at a blocking site on a side of said stimulation site opposite the target organ. The blocking signal is selected to at least partially block nerve impulses to a second organ on a side of said blocking site opposite the stimulation site. In specific examples, the target organ may be gastrointestinal or central nervous with the other organ being cardio-respiratory.

IV. BRIEF DESCRIPTION OF THE DRAWINGS

V. DESCRIPTION OF THE PREFERRED EMBODIMENT

With reference now to the various drawing figures in which identical elements are numbered identically throughout, a description of the preferred embodiment of the present invention will now be described.

A. Invention of Parent Application

Figure 1:
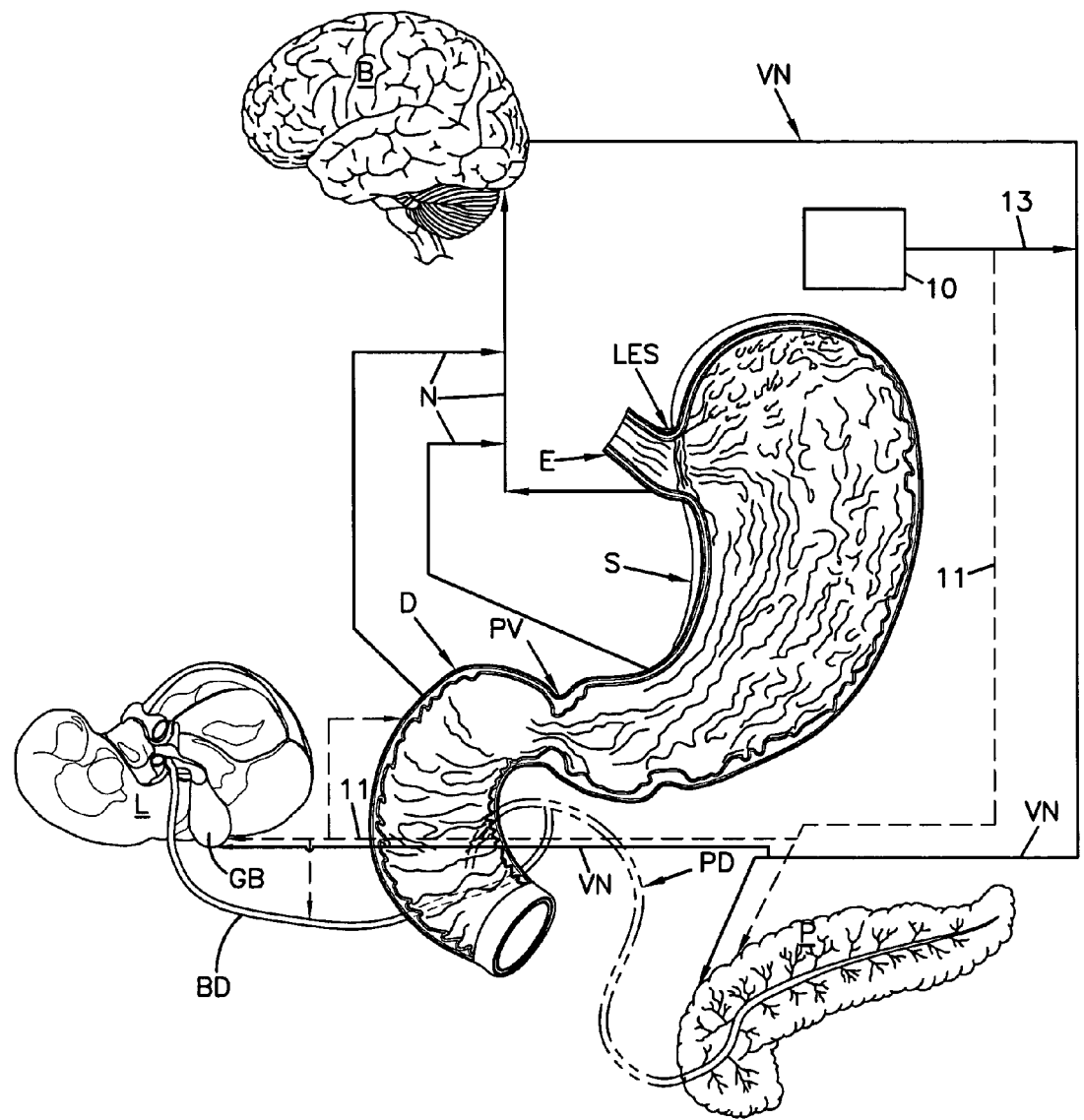
FIG. 1 is a schematic representation of a gastric-emptying feedback loop with a patient-controlled stimulator for stimulating an organ of the loop.
Figure 2:
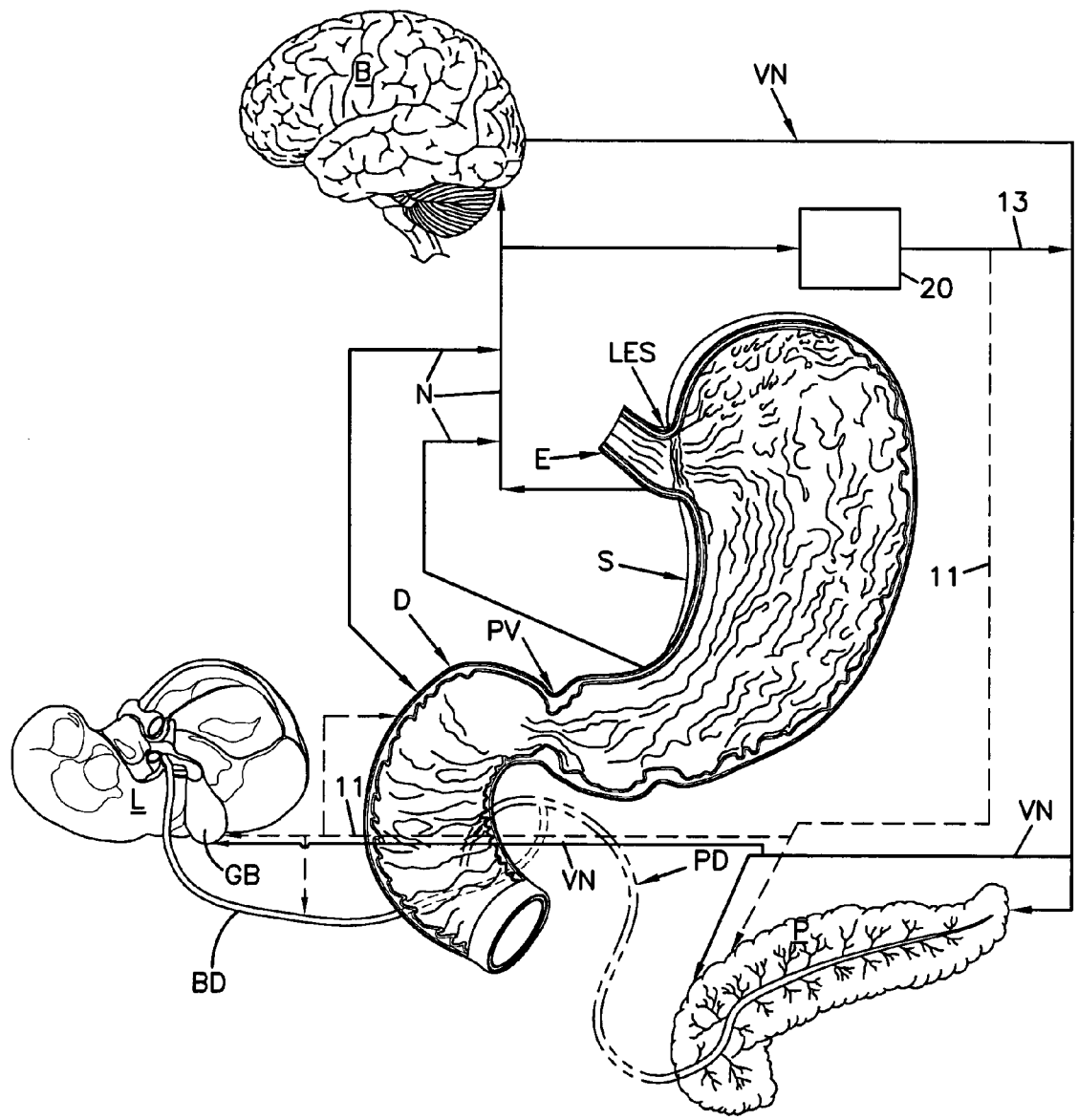
FIG. 2 is a view similar to FIG. 1 with an automatic controller replacing the patient-controller of FIG. 1 and with feedback circuits to the automatic controller schematically represented.

FIGS. 1 and 2 and the description which follow are from the aforementioned U.S. patent application Ser. No. 10/358, 093 filed Feb. 3, 2003 and entitled "Method and Apparatus for Treatment of Gastroesophageal Disease (GERD)".

With initial reference to FIG. 1, a gastric emptying feedback loop is shown schematically for ease of illustration. The feedback loop illustrates a patient's stomach S which is provided with food from the esophagus E. A lower esophageal sphincter LES is shown positioned between the esophagus E and the stomach S. The lower esophageal sphincter normally provides control of reflux of stomach contents into the esophagus E.

On a proximal or lower end of the stomach S the stomach discharges into the superior duodenum D which is an upper portion of the intestines. The superior duodenum D and the stomach S are separated by a pyloric valve PV which opens to permit gastric emptying from the stomach into the duodenum D.

Also schematically illustrated in FIG. 1 are nerve paths N providing signal flow paths from both the superior duodenum D and the stomach S to the brain B. An efferent Vagal nerve VN connects the brain B to the pancreas P of the patient. A conduit (pancreatic duct PD) extends from the pancreas P and discharges into the superior duodenum D.

The presence of food contents within the duodenum D (such contents being referred to as "chyme") may prevent passage of gastric content of the stomach S past the pyloric valve PV into the duodenum D. As long as such gastric contents cannot be passed into the duodenum D, such contents can be forced retrograde past the lower esophageal sphincter LES and into the esophagus E creating the symptoms and discomfort of GERD. The contents discharging from the stomach S into the duodenum D are acidic (and high osmolality) and reside in the duodenum D until pH is elevated (close to a neutral pH of 6-7) and osmolality is normalized.

The elevation of pH and reduction of osmolality of chyme in the duodenum D results from exocrine secretion being administered from the pancreas P and from bile from the liver into the duodenum D. This raises the pH and lowers the osmolality of the duodenum D content permitting discharge from the duodenum D and thereby permitting gastric emptying across the pyloric valve PV.

According to the present invention gastroesophageal reflux disease (GERD) results from a derangement of the feedback loops involved in upper GI digestion and motility control. This problem encompasses receptors and reflexes that regulate the propulsive contractions of the stomach, upper duodenum and biliary tree and the secretions of the exocrine pancreas. The interaction of these receptors and reflexes control gastric emptying (by coordinating gastric propulsive contractions and sphincter [primarily pyloric] tone) and regulate the pH and osmolality of the chyme in the duodenum. This chemo-regulation is mediated through control of bile delivery and stimulation of secretion by the exocrine pancreas of fluid delivered to the superior duodenum. Chey et al., "Neural Hormonal Regulation of Exocrine Pancreatic Secretion", Pancreatology, pp. 320-335 (2001).

Normally, ingestate delivered to the stomach is mixed by low intensity gastric mixing contractions with the enzymatic, ionic, including hydrogen ion ($H^+$), and water secretions of the glands of the stomach. When the material is adequately reduced in size and is a smooth consistency, the fluid, now called chyme, is delivered to the ampulla of the small intestine by the much stronger propulsive, or emptying, contractions of the stomach coupled with transitory relaxation of the pyloric sphincter. This material is at a very low pH (about 2) and high osmolality, which activates receptors, including those for $H^+$ and osmotic pressure, which are abundant in the wall of the ampulla. This receptor activation initiates the series of reflexes that cause pancreatic exocrine secretion to be delivered into the superior duodenum and ampulla. This fluid contains digestive enzymes, water and buffering compounds to raise the pH, and reduce the osmolality, of the chyme.

Once a neutral pH and physiological osmolality are achieved, then propulsive contractions in the superior duodenum move the chyme out of the superior portion into the length of the duodenum; At which point the stretch and baroreceptors in the ampulla allow the pyloric sphincter to relax and another bolus of gastric contents is delivered into the ampulla by the peristaltic gastric emptying contractions. This material, at a very low pH (less than 2), activates hydrogen ion ($H^+$) on receptors of the ampulla (upper most portion of the duodenum) causing the pancreatic fluids to be delivered to the material in the ampulla restarting the cycle as described above. Chapter 3, "The Stomach", Gastrointestinal System, $2^{nd}$ Ed., M. S. Long editor, Mosby Publisher, London (2002).

If the control system is down regulated by, for example, by increased pH of gastric contents entering the ampulla, feedback may thereby be reduced from the $H^+$ receptors in the duodenum that stimulate pancreatic exocrine secretion and bile delivery to the duodenum, then movement of chyme from the superior duodenum is delayed, causing delay of gastric emptying. Mabayo, et al., "Inhibition of Food Passage by Osmeprazole in the Chicken", European J. of Pharmacology, pp. 161-165 (1995).

In GERD, this reflex is inhibited in such a way that the stomach empties more slowly so that the gastric emptying contractions force gastric contents to flow retrograde into the esophagus. This is a result of the situation in which the gastric emptying contractions are vigorous but must operate against a contracted pyloric sphincter. These vigorous peristaltic contractions eventually begin to force gastric contents to flow retrograde into the esophagus because of the inherent imbalance between a very strong pyloric sphincter and a much weaker gastroesophageal sphincter. The delay in gastric emptying is directly related to a slow down in the transport of chyme out of the ampulla and superior duodenum. The drugs used to treat this disease raise pH further dampening the hydrogen-receptor-pancreatic secretion loop, further delaying gastric emptying. Benini, "Gastric Emptying and Dyspeptic Symptoms in Patients with Gastroesophageal Reflux", Amer. J. of Gastroenterology, pp. 1351-1354 (1996).

The present invention is directed towards reestablishing the link between gastric emptying and pancreatic secretion delivery, thereby addressing the main pathology of this disease by shortening chyme residence time in the superior duodenum so that intestinal contents move into the distal digestive tract in a more normal manner. According to a first embodiment, this is done by stimulating the H+ ion receptors or by stimulation of the pancreas directly or via its parasympathetic innervation (pre-ganglionic Vagal nerves). Stimulation of pancreatic exocrine secretion has been shown by direct stimulation of the thoracic vagus nerves in dogs. Kaminski et al., "The Effect of Electrical Vagal Stimulation on Canine Pancreatic Exocrine Function", Surgery, pp. 545-552 (1975). This results in a more rapid (normal) neutralization of chyme in the ampulla, allowing it to move down the duodenum more quickly so that gastric emptying is returned to a more normal pace.

Acidity (pH) can be assessed by measuring bicarbonate. It will be understood that references to —H include such indirect measurements. Also, effects of the therapy described herein can be assessed and/or controlled by measuring an indication of pancreatic exocrine secretion or bile (e.g., $HCO_3^-$).

An alternative embodiment uses gastrocopic delivery of a paralyzing agent (e.g. botulism toxin) to the pyloric valve along with use of H2 antagonists or PPI's to manage the acidity of the chyme reaching the duodenum.

As an additional alternative to pancreatic stimulation, the gall bladder can be stimulated to encourage bile movement into the duodenum. Shown schematically in the figures, the gall bladder GB resides below the liver L. The gall bladder is connected to the small intestine (specifically the duodenum D) via a bile duct BD. The bile duct BD can discharge directly into the duodenum D or via the pancreatic duct PD as shown. The bile can normalize the chyme to accelerate duodenal emptying. Bile consists of bile acids (detergents that emulsify lipids), cholesterol, phospholipids, electrolytes such as ($Na^+$, $K^+$, $Ca^{+2}$, $Cl^-$, $HCO_3^-$) and $H_2O$. Chapter 4, "The Liver and Biliary Tract", Gastrointestinal System, $2^{nd}$ Ed., M. S. Long editor, Mosby Publisher, London (2002). The gall bladder GB or bile duct can be stimulated indirectly via stimulation of the vagal nerve VN or directly stimulated by an electrode 11 (shown in phantom lines).

As illustrated in the figures, an electrical stimulator 10, 20 which may be implanted is provided which alternatively may be directly connected to the Vagal nerve VN or the pancreas P to stimulate the pancreas directly or indirectly to excrete exocrine into the duodenum D (or more distally into the small intestine—e.g., into the jejunum) and increase the pH of chyme in the duodenum D as described. Alternatively, the same can be done to promote bile release. The frequency may be varied to maximize the response and selectively stimulate exocrine instead of endocrine secretions. Rösch et al., "Frequency-Dependent Secretion of Pancreatic Amylase, Lipase, Trypsin, and Chymotrypsin During Vagal Stimulation in Rats", *Pancreas*, pp. 499-506 (1990). See, also, Berthoud et al., "Characteristics of Gastric and Pancreatic Reponses to Vagal Stimulation with Varied Frequencies: Evidence for Different Fiber Calibers?", *J. Auto. Nervous Sys.*, pp. 77-84 (1987) (showed frequency-response relationship with insulin, i.e., significantly less insulin was released at lower frequencies—2 Hz v. 8 Hz—also, frequency-response curves evidenced distinctly different profiles for gastric, pancreatic and cardiovascular responses.) Slight insulin release can maximize pancreatic exocrine secretion. Chey et al., "Neural Hormonal Regulation of Exocrine Pancreatic Secretion", *Pancreatology*, pp. 320-335 (2001).

With a patient control stimulation as shown in FIG. 1, the patient may activate the stimulator 10 by remote transmitter to stimulate an electrical charge either after eating (e.g., about 60 to 90 minutes after eating) or on onset of GERD symptoms. It will be appreciated that there are a wide variety of nerve stimulators and organ stimulators available for implantation and are commercially available and which include connectors for connecting directly to nerves.

FIG. 2 illustrates an additional embodiment where the patient activated loop is replaced with an automatic loop having a programmable stimulator 20 which receives as an input signals from sensors in the duodenum to measure pH, osmolality or strain (e.g., from baro-sensors) on the duodenum indicating filling or may measure acidity in the esophagus or strain on the lower esophageal sphincter LES or stomach S all of which may be provided to the implantable controller 20 which can be provided with desirable software to process the incoming signals and generate a stimulating signal to either the vagal nerve, the pancreas P or the duodenum D (or jejunum) directly in response to such received signals. It will be appreciated that stimulators and controllers are well within the skill of the art. U.S. Pat. No. 5,540,730 teaches a neurostimulator to stimulate a vagus nerve to treat a motility disorder. U.S. Pat. No. 5,292,344 teaches gastrointestinal sensors, including pH sensors.

B. Application of Parent Application to Treatments Other than GERD

In addition to treatment of GERD, the foregoing invention is applicable to treatment of a plurality of GI diseases associated with delayed gastric emptying or altered autonomic activity. These include functional gastrointestinal disorders and gastroparesis. Furthermore, applicants have determined that duodenal content impacts a plurality of motility disorders throughout the bowels and can diseases associated with dysmotility (e.g., irritable bowel syndrome). Accordingly it is an object of the present invention to use the teachings of the aforementioned parent application to treat GI disorders associated with delayed gastric emptying and abnormal intestinal transport.

C. Additional Disclosure of the Present Application

1. Enteric Innervation

Figure 3:
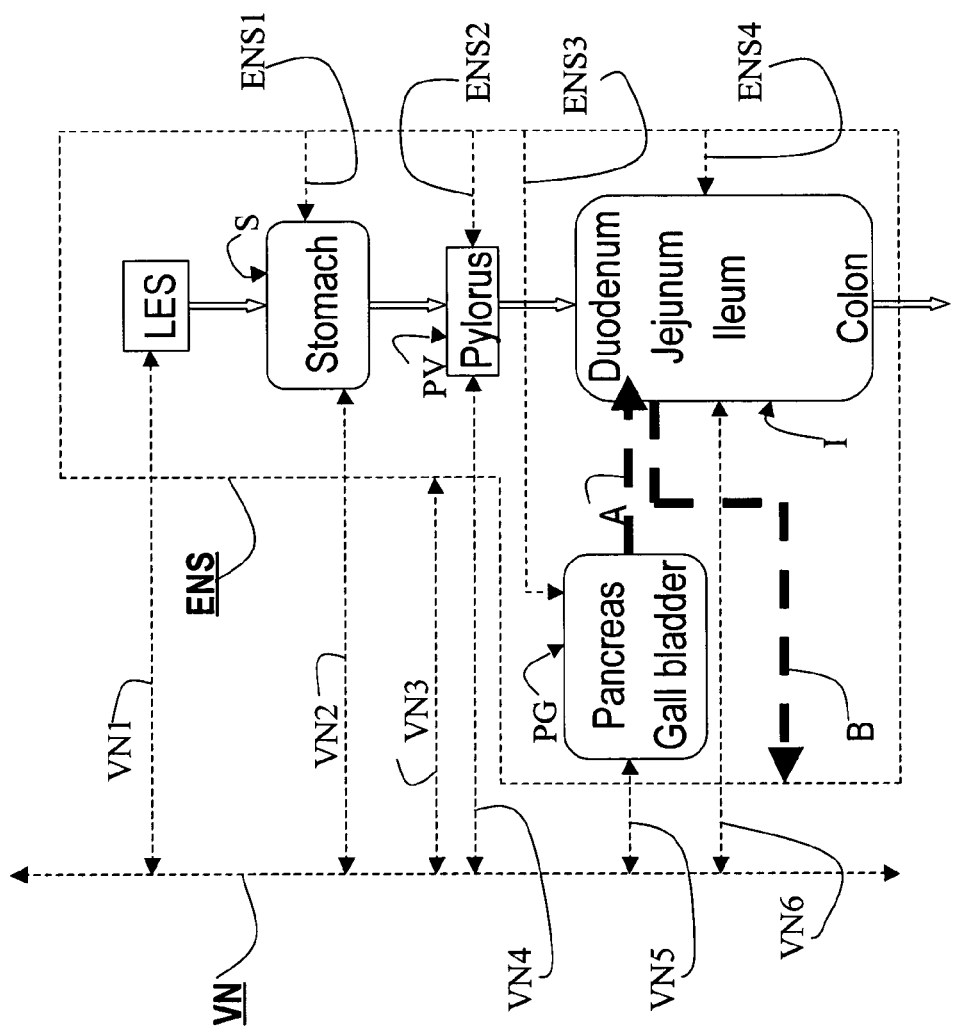
FIG. 3 is a schematic illustration of an alimentary tract (GI tract plus non-GI organs such as the pancreas and liver) and its relation to vagal and enteric innervation.

FIG. 3 is a schematic illustration of an alimentary tract (GI tract plus non-GI organs such as the pancreas and ball bladder, collectively labeled PG) and its relation to vagal and enteric innervation. The lower esophageal sphincter (LES) acts as a gate to pass food into the stomach S and, assuming adequate function of all components, prevent reflux. The pylorus PV controls passage of chyme from the stomach S into the intestines I (collectively shown in the figures and including the large intestine or colon and the small intestine including the duodenum, jejunum and ileum).

The biochemistry of the contents of the intestines I is influenced by the pancreas P and gall bladder PG which discharge into the duodenum. This discharge is illustrated by dotted arrow A.

The vagus nerve VN transmits signals to the stomach S, pylorus PV, pancreas and gall bladder PG directly. Originating in the brain, there is a common vagus nerve VN in the region of the diaphragm (not shown). In the region of the diaphragm, the vagus VN separates into anterior and posterior components with both acting to innervate the GI tract. In FIGS. 3, 5-8, the anterior and posterior vagus nerves are not shown separately. Instead, the vagus nerve VN is shown schematically to include both anterior and posterior nerves.

The vagus nerve VN contains both afferent and efferent components sending signals away from and to, respectively, its innervated organs.

In addition to influence from the vagus nerve VN, the GI and alimentary tracts are greatly influenced by the enteric nervous system ENS. The enteric nervous system ENS is an interconnected network of nerves, receptors and actuators throughout the GI tract. There are many millions of nerve endings of the enteric nervous system ENS in the tissues of the GI organs. For ease of illustration, the enteric nervous system ENS is illustrated as a line enveloping the organs innervated by the enteric nervous system ENS The vagus nerve VN innervates, at least in part, the enteric nervous system ENS (schematically illustrated by vagal trunk VN3 which represents many vagus-ENS innervation throughout the cut). Also, receptors in the intestines I connect to the enteric nervous system ENS. Arrow B in the figures illustrates the influence of duodenal contents on the enteric nervous system ENS as a feedback to the secretion function of the pancreas, liver and gall bladder. Specifically, receptors in the intestine I respond the biochemistry of the intestine contents (which are chemically modulated by the pancreao-biliary output of Arrow A). This biochemistry includes pH and osmolality.

In the figures, vagal trunks VN1, VN2, VN4 and VN6 illustrate schematically the direct vagal innervation of the GI organs of the LES, stomach S, pylorus PV and intestines I. Trunk VN3 illustrates direct communication between the vagus VN and the ENS. Trunk VN5 illustrates direct vagal innervation of the pancreas and gall bladder. Enteric nerves ENS1-ENS4 represent the multitude of enteric nerves in the stomach S, pylorus PV, pancreas and gall bladder PG and intestines I.

While communicating with the vagus nerve VN, the enteric nervous system ENS can act independently of the vagus and the central nervous system. For example, in patients with a severed vagus nerve (vagotomy—an historical procedure for treating ulcers), the enteric nervous system can operate the gut. Most enteric nerve cells are not directly innervated by the vagus. Gershon, "The Second Brain", Harper Collins Publishers, Inc, New York, N.Y. p. 19 (1998)

In FIG. 3, the vagus VN and its trunks (illustrated as VN1-VN6) and the enteric nervous system ENS are shown in phantom lines to illustrate reduced vagal and enteric nerve tone (i.e., sub-optimal nerve transmission levels). Reduced vagal and enteric tone contribute directly to the ineffectiveness of the GI organs as well as indirectly (through reduced pancreatic/biliary output). The reduced pancreatic/biliary output is illustrated by the dotted presentation of arrow A. As previously discussed, the vagus can be stimulated to stimulate pancreatic or biliary output. Therefore, the reduced output of arrow A results in a reduced feedback illustrated by the dotted presentation of arrow B.

2. Enteric Rhythm Management (ERM)

Figure 4:
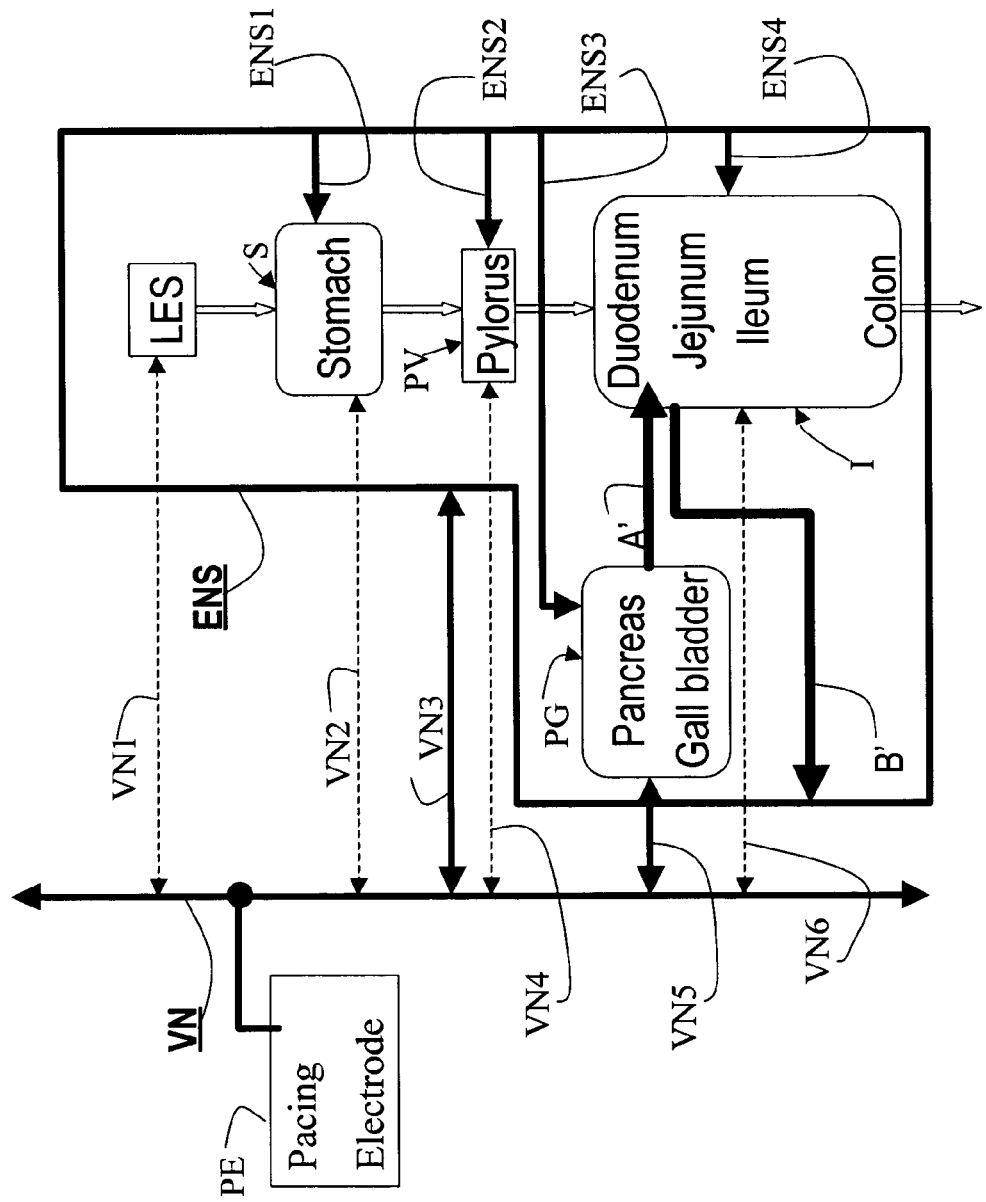
FIG. 4 is the view of FIG. 3 showing the application of a pacing electrode according to an embodiment of the present invention.

The benefits of the present invention are illustrated in FIG. 4 where a stimulating or pacing electrode PE is applied to the vagus VN. While only one electrode is shown in FIG. 4, separate electrodes could be applied to both the anterior and posterior vagus nerves (or to the common vagus or vagal branches). In a preferred embodiment, the electrode PE is placed a few centimeters below the diaphragm and proximal to stomach and pancreo/biliary innervation. While this placement is presently preferred for ease of surgical access, other placement locations may be used.

By pacing the vagus through the pacing electrode, vagal tone is optimized by either up- or down-regulation. With reference to the parasympathetic and enteric nervous systems, "tone" refers to basal activity of a nerve or nervous system facilitating appropriate physiologic response to a patient's internal environment. For example, low vagal tone implies a reduction in vagus nerve activity resulting in decreased response of the alimentary tract to ingested food. As used in the present application, "pacing" is not limited to mean timed events coordinated with specifically timed physiologic events. Instead, pacing means any electrical stimulation of a nerve trunk to induce bi-directional propagation of nervous impulses in the stimulated nerve.

The operating effectiveness of the vagus is enhanced so that local physiological signals generated in the enteric nervous system (or sent to the brain from the organs) are more appropriately responded to within the alimentary tract. Due to its innervation of the enteric nervous system, pacing of the vagus enhances the functional tone of the enteric nervous system. By enhancing the functional tone it will be noted that the stimulation pacing is elevating the degree of functionality of the vagus and enteric nerves. In this context, "pacing" is not meant to mean timed pulsed coordinated with muscular contractions or synchronized with other invents. Pacing means elevating the activity level of the nerves.

Tonal enhancement of the vagus and enteric nerves is illustrated by the solid lines for the nerves VN, ENS in FIG. 4. Vagal trunk VN5 is in solid line to illustrate enhanced tone of the many vagal nerve components communicating with the enteric nervous system ENS. Direct vagal innervation of the LES, stomach S, pylorus PV and intestines I remains shown as low tone indicated by phantom lines VN1, VN2, VN4, VN6. The tonal pacing described herein is not intended to trigger or drive the muscular contractility of these organs. The stimulation is not intended to be timed to trigger contractility and is not provided with an energy level sufficient to drive peristaltic contractions. Instead, these functions remain controlled by the central and enteric nerves systems. The enhanced nerve tone provided by the present invention permits these functions to occur.

Pacing to enhance vagal tone is not initiated in response to any senses event (or in anticipation of an immediate need to GI activity). Instead, the pacing can be done intermittently over the day to provide an enhanced level of operating functionality to the vagus. By way of non-limiting example, the stimulation pacing can be done during awake hours. For example, every ten minutes, pacing signals can be sent to the pacing electrodes. The pacing signals have a duration of 30 seconds with a current of 4 mA, a frequency of 12 Hz and an impulse duration of 2 msec. These parameters are representative only. A wide range of signal parameters may be used to stimulate the vagus nerve. Examples of these are recited in the afore-referenced literature As will be further discussed, the present invention permits ERM to be uniquely designed and modified by an attending physician to meet the specific needs of individual patients. For example, pacing can be limited to discrete intervals in the morning, afternoon and evening with the patient free to coordinate meals around these events.

In addition to enhancing vagal and enteric tone directly, the pacing also enhances the pancreatic and biliary output for the reasons discussed above. Namely, while ERM does not drive muscular events over nerve trunks VN1, VN2, VN4, VN6, the enhanced tone stimulates pancreo-biliary output over trunk VN5 (illustrated by the solid line of VN5 in FIG. 4). This enhanced output is illustrated as solid arrow A' in FIG. 4. As a consequence there is a greater feedback to the intestinal receptors as illustrated by solid arrow B' in FIG. 4. This enhanced biochemistry feedback further enhances the tone of the enteric nervous system ENS.

3. Implantable Pacing Circuit

Figure 5:
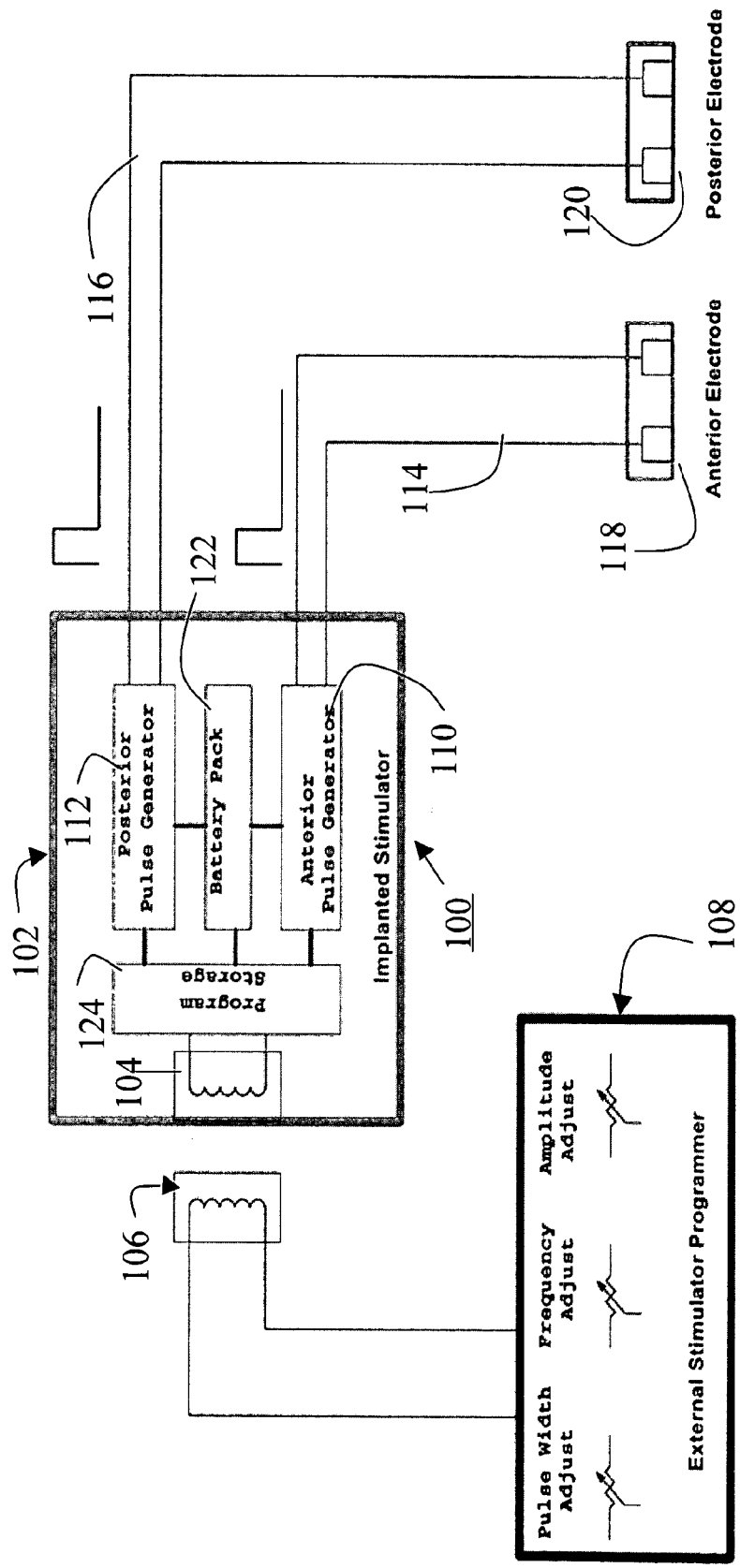
FIG. 5 is a schematic representation of pacing system.

A representative pacing circuit 100 is schematically shown in FIG. 5. Similar to cardiac pacing devices, an implantable controller 102 contains an induction coil 104 for inductive electrical coupling to a coil 106 of an external controller 108. The implantable controller 102 includes anterior and posterior pulse generators 110, 112 electrically connected through conductors 114, 116 to anterior and posterior pacing electrodes 118, 120 for attachment to anterior and posterior trunks, respectively, of the vagus nerve VN. The implantable controller 102 also includes a battery 122 and a CPU 124 which includes program storage and memory. The timing and parameters of the pulse at the electrodes 118, 120 can be adjusted by inductively coupling the external controller 108 to the implantable controller 102 and inputting pacing parameters (e.g., pulse width, frequency and amplitude).

While a fully implantable controller 102 is desirable, it is not necessary. For example, the electrodes 118, 120 can be implanted connected to a receiving antenna placed near the body surface. The control circuits (i.e., the elements 124, 110, 112 and 108) can be housed in an external pack worn by the patient with a transmitting antenna held in place on the skin over the area of the implanted receiving antenna. Such a design is forward-compatible in that the implanted electrodes can be later substituted with the implantable controller 102 at a later surgery if desired.

Although not shown in FIG. 5, the controller 102 can also include circuits generating nerve conduction block signals (as will be described) which connect to electrodes which may be positioned on a nerve proximally, distally (or both) of the electrodes 118, 120.

4. Nerve Conduction Block

Figure 6:
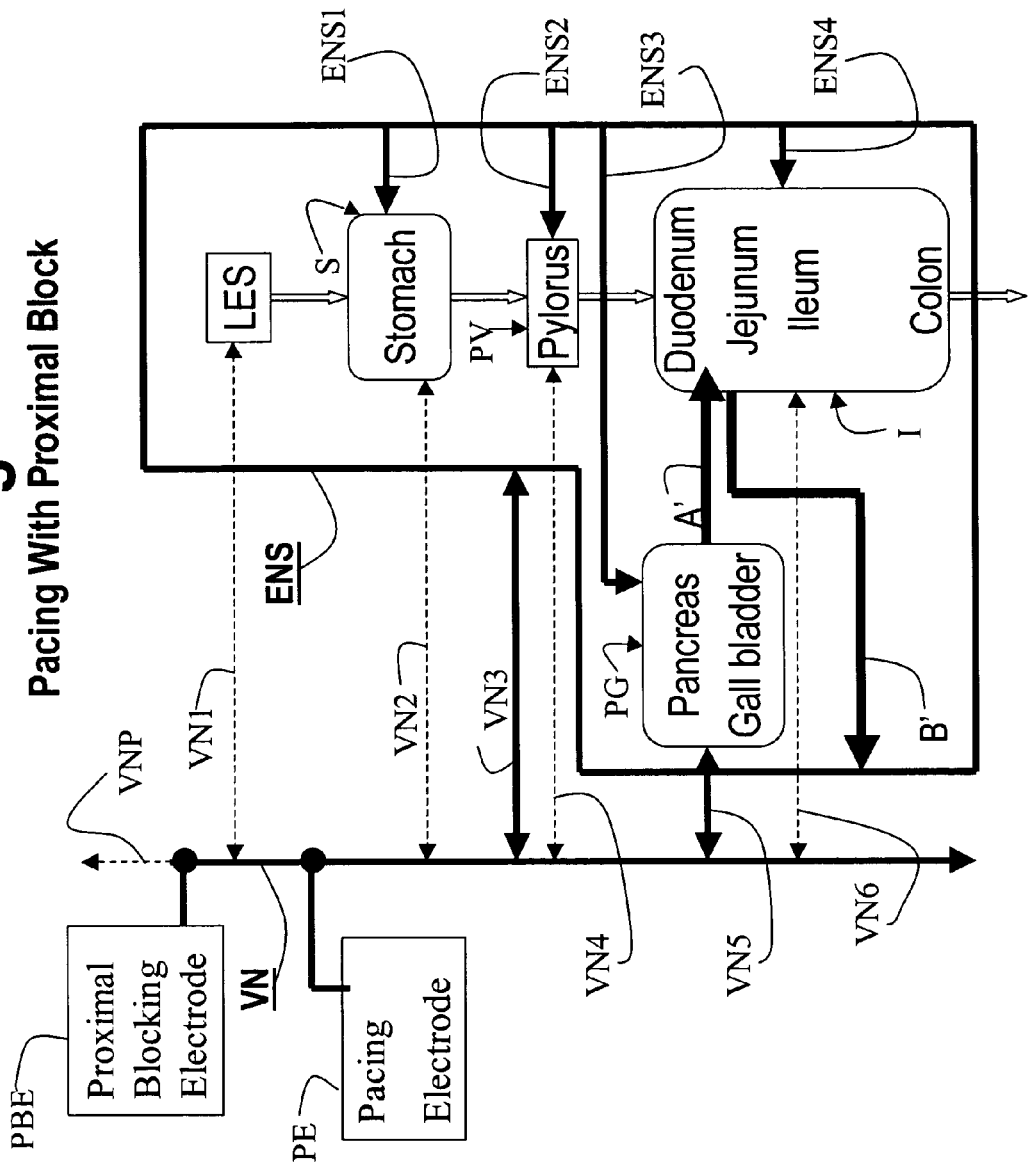
FIG. 6 is the view of FIG. 4 showing the application of a nerve conduction block electrode proximal to the pacing electrode.

FIG. 6 shows an alternative embodiment using a nerve conduction blocking electrode PBE proximal to the pacing electrode for providing a conduction block. A nerve block is, functionally speaking, a reversible vagotomy. Namely, application of the block at least partially prevents nerve transmission across the site of the block. Removal of the block restores normal nerve activity at the site. A block is any localized imposition of conditions that at least partially diminish transmission of impulses.

The vagal block may be desirable in some patients since unblocked pacing may result in afferent vagal and antidromic efferent signals having undesired effect on organs innervated by the vagus proximal to the GI tract (e.g., undesirable cardiac response). Further, the afferent signals of the pacing electrode PE can result in a central nervous system response that tends to offset the benefits of the pacing electrode on the ENS and pancreo/biliary function, thereby reducing the GI and enteric rhythm management effectiveness of vagal pacing.

The block may be intermittent and applied only when the vagus is paced by the pacing electrode PE. The preferred nerve conduction block is an electronic block created by a signal at the vagus by an electrode PBE controlled by the implantable controller (such as controller 102 or an external controller). The nerve conduction block can be any reversible block. For example, cryogenics (either chemically or electronically induced) or drug blocks can be used. An electronic cryogenic block may be a Peltier solid-state device which cools in response to a current and may be electrically controlled to regulate cooling. Drug blocks may include a pump-controlled subcutaneous drug delivery.

With such an electrode conduction block, the block parameters (signal type and timing) can be altered by a controller and can be coordinated with the pacing signals to block only during pacing. A representative blocking signal is a 500 Hz signal with other parameters (e.g., timing and current) matched to be the same as the pacing signal). While an alternating current blocking signal is described, a direct current (e.g., −70 mV DC) could be used. The foregoing specific examples of blocking signals are representative only. Other examples and ranges of blocking signals are described in the afore-mentioned literature (all incorporated herein by reference). As will be more fully described, the present invention gives a physician great latitude in selected pacing and blocking parameters for individual patients.

Similar to FIG. 4, the vagus VN and enteric nervous system ENS in FIG. 6 distal to the block PBE are shown in solid lines to illustrate enhanced tone (except for the direct innervation VN1, VN2, VN4, VN6 to the GI tract organs). Similarly, arrows A', B' are shown in solid lines to illustrate the enhanced pancreo-biliary output and resultant enhanced feedback stimulation to the enteric nervous system ENS. The proximal vagus nerve segment VNP proximal to the block PBE is shown in phantom lines to illustrate it is not stimulated by the pacing electrode PE while the blocking electrode PBE is activated.

5. Proximal and Distal Blocking

Figure 7:
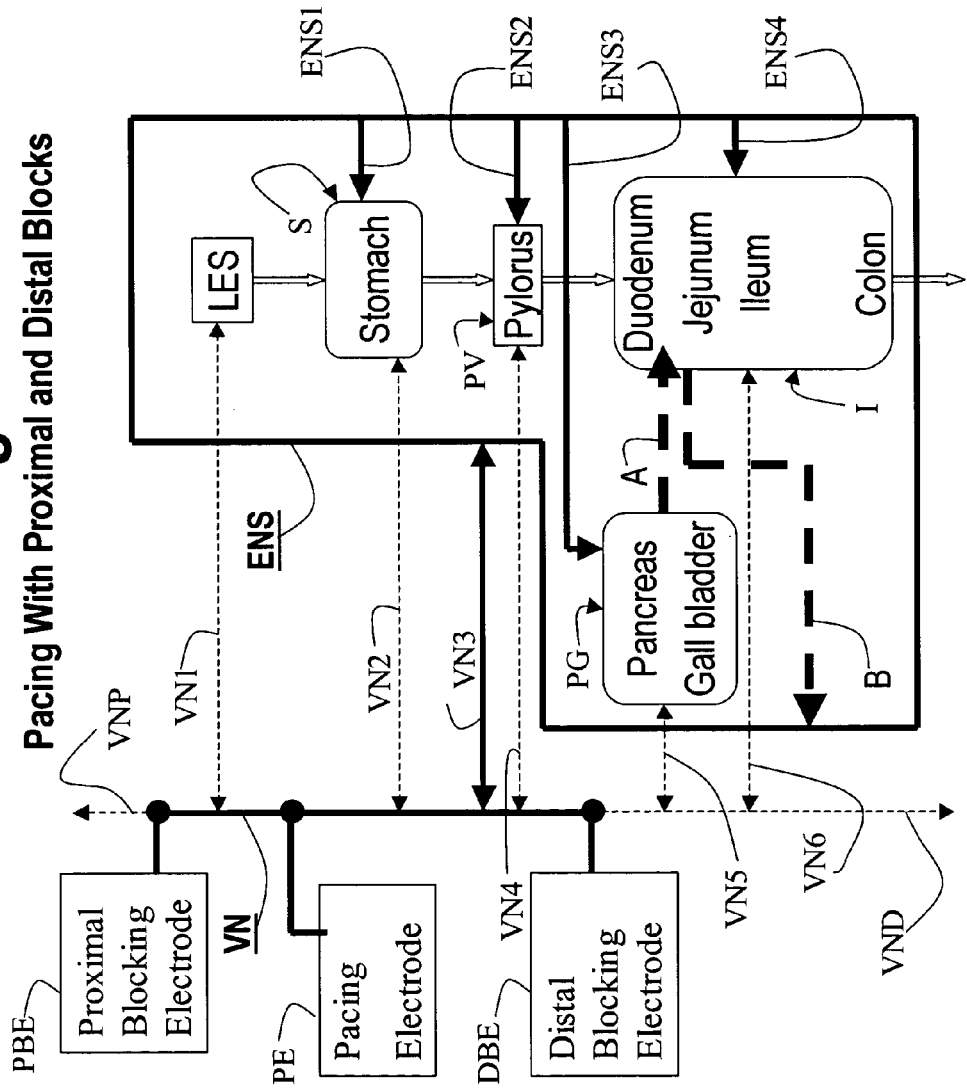
FIG. 7 is the view of FIG. 6 showing the application of a nerve conduction block electrode distal to the pacing electrode.

FIG. 7 illustrates the addition over FIG. 6 of a nerve conductive block DBE distal to the pacing electrode PE. The proximal block PBE prevents adverse events resulting from afferent signals and heightens the GI effectiveness by blocking antidromic interference as discussed with reference to FIG. 6.

In FIG. 7, the distal block DBE is provided in the event there is a desire to isolate the pacing effect of electrode PE. For example, a physician may which to enhance the vagus and enteric activity in the region proximal to the duodenum but may wish to avoid stimulating pancreo-biliary output. For example, a patient may have a GI problem without apparent colon dysfunction (e.g., gastroparesis functional dyspepsia without bowel symptoms). Placing the distal block DBE on a branch of the vagus between the pacing electrode PE and the pancreas and gall bladder PG prevents increased pancreo-biliary output and resultant feedback (illustrated by dotted arrows A and B in FIG. 7 and dotted distal vagal nerve segment VND and vagal trunk VN5).

6. Blocking As an Independent Therapy

Figure 8:
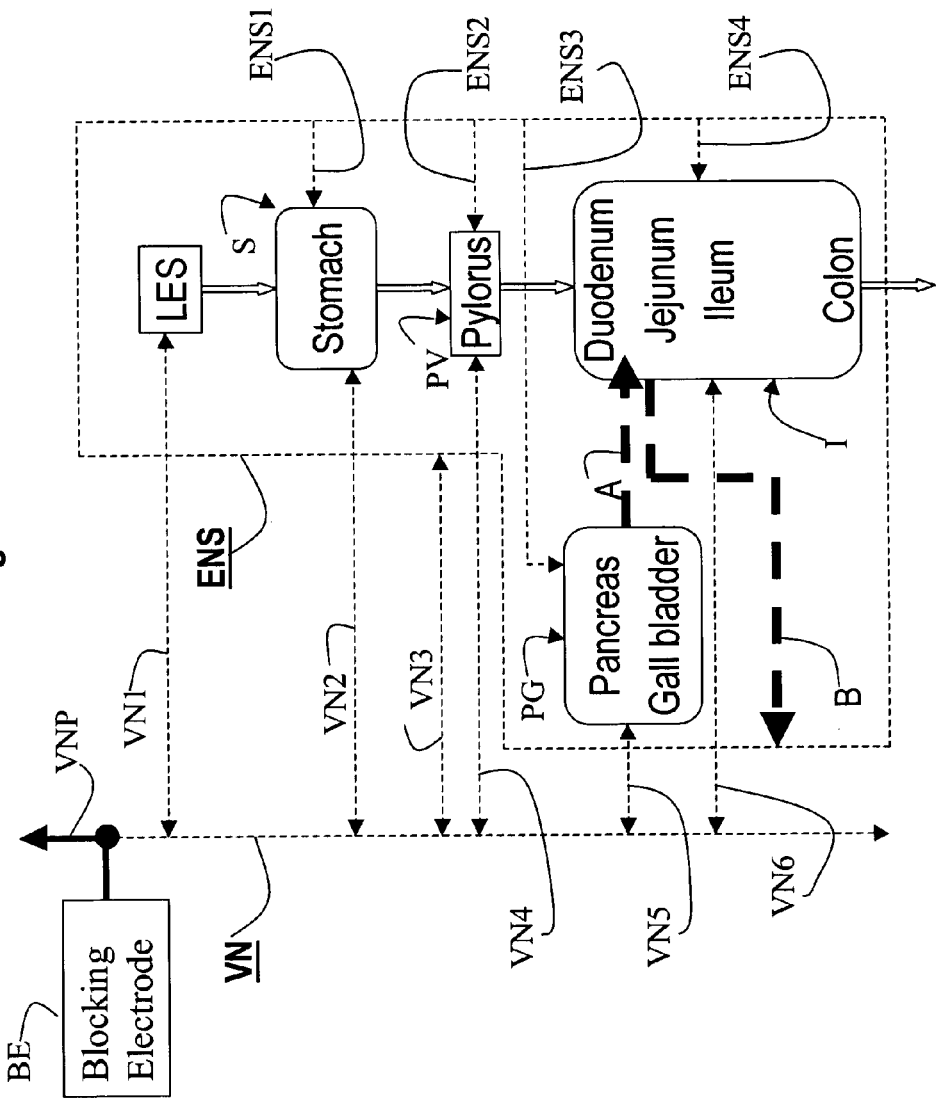
FIG. 8 is the view of FIG. 3 showing the application of a nerve conduction block electrode according to an embodiment of the present invention.

FIG. 8 illustrates an alternative embodiment of the invention.

In certain patients, the vagus nerve may be hyperactive contributing to diarrhea-dominant IBS. Use of a blocking electrode alone in the vagus permits down-regulating the vagus nerve VN, the enteric nervous system ENS and pancreo-biliary output. The block down-regulates efferent signal transmission. In FIG. 8, the hyperactive vagus is illustrated by the solid line of the proximal vagus nerve segment VNP. The remainder of the vagus and enteric nervous system are shown in reduced thickness to illustrate down-regulation of tone. The pancreo-biliary output (and resulting feedback) is also reduced. In FIG. 8, the blocking electrode BE is shown high on the vagus relative to the GI tract innervation (e.g., just below the diaphragm), the sole blocking electrode could be placed lower (e.g., just proximal to pancreo/biliary innervation VN5).

7. Application to Obesity

The foregoing discussion has been described in a preferred embodiment of treating FGIDs, gastroparesis and GERD. Obesity is also treatable with the present invention.

Recent literature describes potential obesity treatments relative to gut hormone fragment peptide $YY_{3-36}$. See, e.g., Batterham, et al., "Inhibition of Food Intake in Obese Subjects by Peptide YY3-36", *New England J. Med.*, pp. 941-948 (Sep. 4, 2003) and Korner et al., "To Eat or Not to Eat—How the Gut Talks to the Brain", *New England J. Med.*, pp. 926-928 (Sep. 4, 2003). The peptide $YY_{3-36}$ (PPY) has the effect of inhibiting gut motility through the phenomena of the ileal brake. Vagal afferents create a sensation of satiety.

The present invention can electrically simulate the effects of PPY by using the vagal block to down-regulate afferent vagal activity to create a desired sensation of satiety. Since the down-regulation does not require continuous blocking signals, the beneficial efferent signals are permitted.

8. Application to Other Therapies

There are numerous suggestions for vagal pacing or stimulation to treat a wide variety of diseases. For example, U.S. Pat. No. 5,188,104 dated Feb. 23, 1993 describes vagal stimulation to treat eating disorders. U.S. Pat. No. 5,231,988 dated Aug. 3, 1993 describes vagal stimulation to treat endocrine disorders. U.S. Pat. No. 5,215,086 dated Jun. 1, 1993 describes vagal stimulation to treat migraines. U.S. Pat. No. 5,269,303 dated Dec. 14, 1993 describes vagal stimulation to treat dementia. U.S. Pat. No. 5,330,515 dated Jul. 19, 1994 describes vagal stimulation to treat pain. U.S. Pat. No. 5,299,569 dated Apr. 5, 1994 describes vagal stimulation to treat neuropsychiatric disorders. U.S. Pat. No. 5,335,657 dated Aug. 9, 1994 describes vagal stimulation to treat sleep disorders. U.S. Pat. No. 5,707,400 dated Jan. 13, 1998 describes vagal stimulation to treat refractory hypertension. U.S. Pat. No. 6,473,644 dated Oct. 29, 2002 describes vagal stimulation to treat heart failure. U.S. Pat. No. 5,571,150 dated Nov. 5, 1996 describes vagal stimulation to treat patients in comas. As previously described, U.S. Pat. No. 5,540,730 dated Jul. 30, 1996 describes vagal stimulation to treat motility disorders and U.S. Pat. No. 6,610,713 dated Aug. 26, 2003 describes vagal stimulation to inhibit inflammatory cytokine production. All of the foregoing U.S. patents listed in this paragraph are incorporated herein by reference.

All of the foregoing suffer from undesired effects of vagal pacing on cardiovascular, gastrointestinal or other organs. Nerve conduction blocking permits longer pulse durations which would otherwise have adverse effects on other organs such as those of the cardiovascular or gastrointestinal systems. In accordance with the present invention, all of the foregoing disclosures can be modified by applying a blocking electrode and blocking signal as disclosed herein to prevent adverse side effects. By way of specific example, pacing a vagus nerve in the thoracic cavity or neck combined with a blocking electrode on the vagus nerve distal to the pacing electrode can be used to treat neuropsychiatric disorders (such as depression and schizophrenia) and Parkinson's and epilepsy and dementia. In such treatments, the blocking electrode is placed distal to the stimulating electrode 25 shown in FIGS. 4 and 2, respectively, of each of U.S. Pat. Nos. 5,269,303 and 5,299,569. The present invention thereby enables the teachings of the afore-referenced patents listed in foregoing two paragraphs.

As described, the parameters of the stimulating and blocking electrodes can be inputted via a controller and, thereby, modified by a physician. Also, FIG. 2 illustrates a feedback for controlling a stimulating electrode. Feedbacks for stimulating electrodes are also described in the patents incorporated by reference. The blocking electrode can also be controlled by an implanted controller and feedback system. For example, physiologic parameters (e.g., heart rate, blood pressure, etc.) can be monitored. The blocking signal can be regulated by the controller to maintain measured parameters in a desired range. For example, blocking can be increased to maintain heart rate within a desired rate range during stimulation pacing.

9. Opportunity for Physician to Alter Treatment for Specific Patient

Gastrointestinal disorders are complex. For many, the precise mechanism is of the disorder is unknown. Diagnosis and treatment are often iterative processes. The present invention is particularly desirable for treating such disorders.

Use of proximal and distal blocking electrodes in combination with one or more pacing electrode permits a physician to alter an operating permutation of the electrodes. This permits regional and local up- or down-regulation of the nervous system and organs. Further, pacing parameters (duty cycle, current, frequency, pulse length) can all be adjusted. Therefore, the treating physician has numerous options to alter a treatment to meet the needs of a specific patient.

In addition, a physician can combine the present invention with other therapies (such as drug therapies like prokinetic agents).

With the foregoing detailed description of the present invention, it has been shown how the objects of the invention have been attained in a preferred manner. Modifications and equivalents of disclosed concepts such as those which might readily occur to one skilled in the art, are intended to be included in the scope of the claims which are appended hereto.

We claim:

1. A method for treating obesity of an obese patient by applying a neural treatment comprising:
 applying an electrode to a vagus nerve of the obese patient at a site below a vagal innervation of a heart of the patient to deliver an electrical signal and with the electrical signal applied by a device with a component chronically implanted within the patient's body; and
 applying the electrical signal to the vagus nerve intermittently multiple times in a day and over multiple days, wherein the electrical signal is selected to a) at least partially block at least an afferent neural activity on the vagus nerve without ablating the vagus nerve of the obese patient; b) allow at least partial restoration of nerve activity following discontinuation of application of the signal to the nerve; and c) reduce pancreo-biliary output; wherein the electrical signal is not applied in response to a sensed event.

2. A method according to claim 1 wherein said neural treatment is regulated to heighten a sensation of satiety of said patient.

3. A method according to claim 1 wherein the electrode is applied at a vagal trunk.

4. A method according to claim 1 wherein the electrode is applied at a vagal branch.

5. A method according to claim 1 wherein the electrode is applied at both anterior and posterior vagus nerves of the patient.

6. A method according to claim 1 wherein the electrode is applied at the vagus nerve at a location near or distal to a diaphragm of the patient.

7. A method according to claim 1 wherein the neural treatment is further selected to at least partially block efferent nerve signals.

8. A method for treating obesity in a patient comprising:
 applying a treatment comprising a reversible intermittent electrical signal by placing an electrode on a vagus nerve of the patient at a site below a vagal innervation of a heart of the patient by a device with a component chronically implanted within the patient's body;
 wherein the electrical signal is selected to a) at least partially block at least an afferent neural activity on the vagus nerve of the patient; b) allow at least partial restoration of nerve activity following discontinuation of application of the signal to the nerve; and c) reduce pancreo-biliary output; wherein the electrical signal is not applied in response to a sensed event.

* * * * *